US012674143B2

(12) United States Patent
Nolden

(10) Patent No.: US 12,674,143 B2
(45) Date of Patent: Jul. 7, 2026

(54) VSV RESCUE

(71) Applicant: Boehringer Ingelheim International GmbH, Ingelheim am Rhein (DE)

(72) Inventor: Tobias Nolden, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1034 days.

(21) Appl. No.: 17/811,363

(22) Filed: Jul. 8, 2022

(65) Prior Publication Data

US 2023/0183650 A1 Jun. 15, 2023

(30) Foreign Application Priority Data

Jul. 9, 2021 (EP) ..................................... 21184742

(51) Int. Cl.
*C12N 5/071* (2010.01)
*C12N 15/86* (2006.01)

(52) U.S. Cl.
CPC ........... *C12N 5/0686* (2013.01); *C12N 15/86* (2013.01); *C12N 2760/20241* (2013.01); *C12N 2760/20251* (2013.01)

(58) Field of Classification Search
CPC .................. C12N 5/0686; C12N 15/86; C12N 2760/20241; C12N 2760/20251; C12N 2710/22022; C12N 7/00
See application file for complete search history.

(56) References Cited

FOREIGN PATENT DOCUMENTS

| WO | 2004009768 A2 | 1/2004 |
| WO | 2004113517 A2 | 12/2004 |
| WO | 2010040526 A1 | 4/2010 |
| WO | 2020152306 A1 | 7/2020 |

OTHER PUBLICATIONS

Mahon (2011, Biotechniques, 51:119-127).*
Shimojima (J Vet Med Sci. Oct. 2012; 74(10): 1363-1366).*
Durocher (Journal of Virological Methods 144 (2007) 32-40).*

Arthur, Avril K. et al., "Expression of Simian Virus 40 T Antigen in Escherichia coli: Localization of T-Antigen Origin DNA-Binding Domain to within 129 Amino Acids", Journal of Virology, vol. 62, No. 6, (1988), pp. 1999-2006.
Elahi, Seyyed Mehdy et al., "Optimization of Production of Vesicular Stomatitis Virus (VSV) in Suspension Serum-Free Culture Medium at High Cell Density", Journal of Biotechnology, vol. 289, (2019), pp. 144-149.
Extended European Search Report from EP21184742.1, mailed Feb. 9, 2022, 12 pages.
Li, Hongyue et al., "Establishment of Replication-Competent Vesicular Stomatitis Virus-Based Recombinant Viruses Suitable for SARS-COV-2 Entry and Neutralization Assays", Emerging Microbes & Infections, vol. 9, No. 1, (2020), pp. 2269-2277.
Malm, Magdalena et al., "Evolution From Adherent to Suspension: Systems Biology of HEK293 Cell Line Development", Scientific Reports, vol. 10, No. 1, (2020), pp. 1-15.
Takahashi, Kei et al., "Reversible Gene Regulation in Mammalian Cells Using Riboswitch-Engineered Vesicular Stomatitis Virus Vector", ACS Synthetic Biology, vol. 8, No. 9, (2019), pp. 1976-1982.
Witko, Susan E., "An Efficient Helper-Virus-Free Method for Rescue of Recombinant Paramyxoviruses and Rhadoviruses From a Cell Line Suitable for Vaccine Development", Journal of Virological Methods, vol. 135, No. 1, (2006), pp. 91-101.

* cited by examiner

*Primary Examiner* — Valarie E Bertoglio
(74) *Attorney, Agent, or Firm* — McNeill PLLC

(57) ABSTRACT

The present invention relates to a method for rescue of Vesicular Stomatitis Virus (VSV) from DNA in a HEK293 cell line or a HEK293 cell line adapted to suspension growth comprising (a) providing cells from a HEK293 cell line or a HEK293 cell line adapted to suspension growth in cell culture, (b) transfecting the cells with at least one plasmid, wherein the at least one plasmid comprises (i) an expression cassette comprising a VSV genomic cDNA; (ii) at least one expression cassette encoding VSV nucleoprotein (N) protein, VSV phosphoprotein (P) protein, and VSV large (L) protein; and (iii) an expression cassette encoding SV40 Large T antigen; (c) culturing the transfected cells; and (d) harvesting the cell culture supernatant comprising the rescued VSV. Also provided is the use of a HEK293 cell line or a HEK293 cell line adapted to suspension growth for rescue of Vesicular Stomatitis Virus (VSV) or the use of a plasmid encoding SV40 Large T antigen for rescue of Vesicular Stomatitis Virus (VSV) in a HEK293 cell line or a HEK293 cell line adapted to suspension growth HEK293-F cells by means of transient transfection.

18 Claims, 7 Drawing Sheets

Figure 1:
Figure 1:
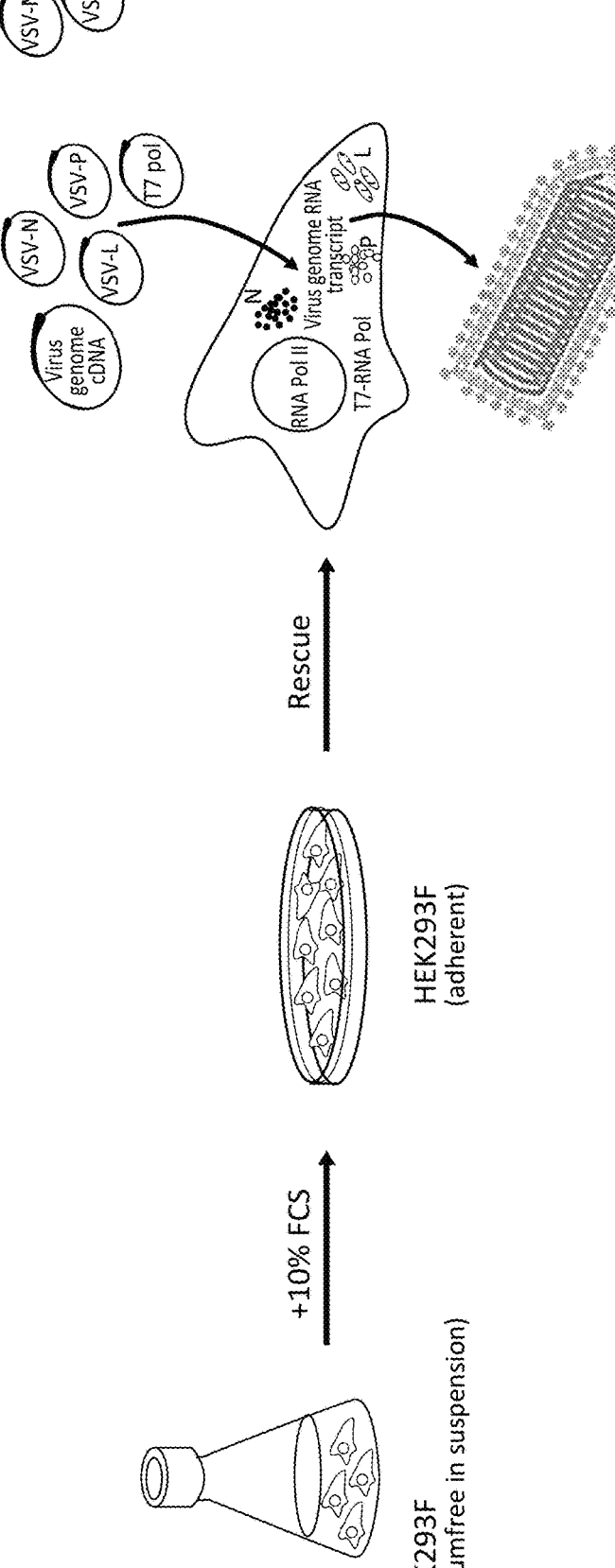

Specification includes a Sequence Listing.

VSV RESCUE

CROSS REFERENCE TO RELATED APPLICATIONS

This application claims priority from European Application No. 21184742.1, filed Jul. 9, 2021, the entire contents of which are incorporated by reference herein for all purposes.

SEQUENCE LISTING

This application contains a Sequence Listing in computer readable form entitled "01251-0011-00US-st26_final.xml" created Jul. 6, 2022, having a size of 25000 bytes, which is incorporated by reference herein.

FIELD OF THE INVENTION

The present invention relates to a method for rescue of Vesicular Stomatitis Virus (VSV) from DNA in a HEK293 cell line or a HEK293 cell line adapted to suspension growth comprising (a) providing cells from a HEK293 cell line or a HEK293 cell line adapted to suspension growth in cell culture, (b) transfecting the cells with at least one plasmid, wherein the at least one plasmid comprises (i) an expression cassette comprising a VSV genomic cDNA; (ii) at least one expression cassette encoding VSV nucleoprotein (N) protein, VSV phosphoprotein (P) protein, and VSV large (L) protein; and (iii) an expression cassette encoding SV40 Large T antigen; (c) culturing the transfected cells; and (d) harvesting the cell culture supernatant comprising the rescued VSV. Also provided is the use of a HEK293 cell line or a HEK293 cell line adapted to suspension growth for rescue of Vesicular Stomatitis Virus (VSV) or the use of a plasmid encoding SV40 Large T antigen for rescue of Vesicular Stomatitis Virus (VSV) in a HEK293 cell line or a HEK293 cell line adapted to suspension growth by means of transient transfection.

BACKGROUND OF THE INVENTION

The vesicular stomatitis virus (VSV) is a negative-sense single-stranded RNA (ssRNA) virus of the order Mononegavirales, which belongs together with the rabies virus to the family Rhabdoviridae. Negative-sense viral RNA is complementary to mRNA and must be converted into positive-sense RNA by an RNA-dependent RNA polymerase before translation. Thus, purified RNA of a negative-sense RNA is not infectious as it needs to be transcribed first, which requires an RNA-dependent RNA polymerase comprised in the virus particle (virion).

The recovery of complete negative-stranded RNA viruses from cloned cDNAs is among the most exciting breakthroughs in RNA virology in the 1990s since it has opened the door to directly engineering of the viral genomes. Thus, the recovery of complete negative-stranded RNA viruses from cloned cDNAs is a prerequisite for the use of recombinant viruses like VSV in clinical settings, such as for gene therapy or as oncolytic virus. It allows to engineer VSV to carry cargo or to modify viral proteins, such as the glycoprotein to change tropism or immune evasion.

Schnell et al., found a key to recovery of non-segmented, negative RNA viruses that had eluded the field for years (Roberts & Rose, Virology, 1998, 247, 1-6; Schnell et al., EMBO J., 1994, 13(18), 4195-4203). The method they described is as follows: Plasmids encoding the viral nucleo protein (N) and the polymerase subunits (L and P) were transfected into cells previously infected with recombinant vaccinia virus expressing the T7 polymerase protein (vTF7-3). In addition to these plasmids, a plasmid encoding a full-length antigenomic viral RNA under the control of a T7 promoter at the 5' end and a self-cleaving ribozyme at the 3'end was also transfected into the cells. After transcription of RNAs from the T7 promoter and translation of the encoded proteins, nucleo protein assemble around the antigenomic RNAs, and polymerase proteins then replicated these ribonucleoprotein (RNPs) to form RNPs containing genomic RNAs. After transcription of mRNA from the genomic RNP and translation, infectious virus is assembled. This procedure led to successful recovery of recombinant rabies virus. In 1995 using a very similar strategy, the first successful recoveries of vesicular stomatitis virus (VSV) from cDNAs were reported (Lawson et al., 1995, Proc. Natl., Acad. Sci, USA 92(10), 4477-4481; Whelan et al., 1995, Proc. Natl., Acad. Sci, USA 92(18), 8388-8392).

Only minor adaptations to this system have been performed in recent years, such as stable expression of the T7 polymerase protein in BHK cells or co-transfection of a plasmid encoding the T7 polymerase protein under the control of a strong promoter. However, while VSV normally has a broad tropism conferred by VSV G, successful recovery of VSV from cDNA is restricted to very few cell lines including BHK cells and HEK293T cells.

Large titers of VSV need to be produced for clinical use and this requires production in suspension culture. The inventors of the present invention found that HEK293 cell lines adapted to suspension growth not susceptible to VSV recovery from cDNA can be rendered susceptible to VSV recovery by transient co-transfection of a plasmid encoding the SV40 large T antigen. This allows VSV rescue from the same cell line used for VSV large scale production.

SUMMARY OF THE INVENTION

The present invention relates to a method for rescue of Vesicular Stomatitis Virus (VSV) from DNA in a HEK293 cell line or a HEK293 cell line adapted to suspension growth comprising (a) providing cells from a HEK293 cell line or a HEK293 cell line adapted to suspension growth in cell culture, (b) transfecting the cells with at least one plasmid, wherein the at least one plasmid comprises (i) an expression cassette comprising a VSV genomic cDNA; (ii) at least one expression cassette encoding VSV nucleoprotein (N) protein, VSV phosphoprotein (P) protein and VSV large (L) protein; and (iii) an expression cassette encoding SV40 Large T antigen; (c) culturing the transfected cells; and (d) harvesting the cell culture supernatant comprising the rescued VSV. Preferably the harvested cell culture supernatant comprises infectious VSV. In certain embodiments, the method may further comprising a step (e) comprising transducing cells from a HEK293 cell line or a HEK293 cell line adapted to suspension growth in suspension with VSV obtained in step (d); and optionally a step (f) comprising producing VSV in the cells of step (e) in suspension culture at large scale, preferably at >50 L. Preferably the HEK293 cell line or HEK293 cell line adapted to suspension growth according to step (e) is the same as cell line as the HEK293 cell line or HEK293 cell line adapted to suspension growth according to step (a).

In certain embodiments (i) the cells are provided, transfected and cultured as adherent cells; (ii) the cells are transiently transfected in step (b); (iii) transfecting the cells in step (b) comprises the use of a chemical-based transfec 3                                                                                                4 tion agent, preferably wherein the chemical-based transfection agent is selected from Lipofection, PEI or calcium phosphate; or any combination of (i), (ii) or (iii).

In certain embodiments the cells in step (b) are further transfected or transduced with a plasmid or a helper virus comprising an expression cassette encoding bacteriophage T7 RNA polymerase under the control of an RNA polymerase II-dependent promoter; and wherein the expression cassette comprising the VSV genomic cDNA comprises the VSV genomic cDNA under the control of a T7 promoter and a T7 terminator sequence; and optionally wherein the at least one expression cassette encoding VSV N protein, VSV P protein and VSV L protein comprises the VSV N, P and/or L protein under the control of a promoter and a terminator sequence. In a preferred embodiment the method is a helper-virus free method, wherein the cells in step (b) are transfected with the plasmid comprising an expression cassette encoding bacteriophage T7 RNA polymerase under the control of an RNA polymerase II-dependent promoter. In certain embodiments the bacteriophage T7 RNA polymerase has the amino acid sequence of SEQ ID NO: 4 or has at least 95% sequence identity with the amino acid sequence or SEQ ID NO: 4. In certain alternative or additional embodiments the nucleotide sequence encoding the bacteriophage T7 RNA polymerase is codon-optimized.

The at least one expression cassette encoding the VSV N protein, VSV P protein and VSV L protein may be transfected as one or more helper plasmids. For example, the one or more helper plasmid comprises (i) a first helper plasmid comprising an expression cassette comprising a sequence encoding the VSV N protein, preferably comprising a sequence encoding the VSV N protein under the control of a promoter and a terminator sequence; (ii) a second helper plasmid comprising an expression cassette comprising a sequence encoding the VSV P protein, preferably comprising a sequence encoding the VSV P protein under the control of a promoter and a terminator sequence; and (iii) a third helper plasmid comprising an expression cassette comprising a sequence encoding the VSV L protein, preferably comprising a sequence encoding the VSV L protein under the control of a promoter and a terminator sequence and (iv) optionally at least one further helper plasmid comprising an expression cassette comprising a sequence encoding VSV glycoprotein (G) and/or an expression cassette comprising a sequence encoding VSV matrix (M) protein, preferably under the control of a promoter and a terminator sequence.

The expression cassette encoding SV40 Large T antigen according to the method of the invention is transfected as a plasmid comprising said expression cassette encoding SV40 Large T antigen and/or comprises the nucleic acid sequence encoding the SV40 Large T antigen under the control of a promoter and further comprises a terminator sequence, preferably under the control of a strong RNA polymerase II-dependent promoter, more preferably a CMV promoter or a CAG promoter. In certain embodiments the expression cassette comprises a nucleic acid sequence encoding the SV40 large T antigen having an amino acid sequence of SEQ ID NO: 5 or having at least 95% sequence identity with the amino acid sequence of SEQ ID NO: 5.

The HEK293 cell line or HEK293 cell line adapted to suspension growth without being limited thereto may be selected from the group consisting of HEK293, HEK293-F, HEK-293-H, Expi293F cells and FreeStyle HEK293-F. Preferably the cells are from a HEK293 cell line adapted to suspension growth, more preferably the cells are from a HEK293 cell line adapted to suspension growth selected from the group consisting of HEK293-F, HEK-293-H, Expi293F and Freestyle HEK293-F. Even more preferably, the cells are HEK293-F cells.

The VSV genomic cDNA according to the method of the invention is a viral full-length genomic cDNA or a modified viral genomic cDNA. In certain embodiments the VSV genomic cDNA is a modified viral genomic cDNA encoding a modified G protein. In certain embodiments the VSV genomic cDNA is a modified viral genomic cDNA encoding a modified G protein, wherein the gene coding for the glycoprotein G in the VSV genomic cDNA is replaced by a gene coding for the glycoprotein GP of Lymphocyte choriomeningitis virus (LCMV); preferably the glycoprotein GP comprises an amino acid sequence as set forth in SEQ ID NO: 7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 7.

In certain embodiments the SV40 large T antigen encoded by the expression cassette in the method according to the invention has the amino acid sequence of SEQ ID NO: 5 or has at least 95% sequence identity with the amino acid sequence of SEQ ID NO: 5.

In another aspect the invention relate to a use of a HEK293 cell line or a HEK293 cell line adapted to suspension growth for rescue of Vesicular Stomatitis Virus (VSV) by means of transient transfection of at least one plasmid comprising (i) an expression cassette comprising a VSV genomic cDNA, and (ii) at least one expression cassette encoding VSV nucleoprotein (N) protein, VSV phosphoprotein (P) protein and VSV large (L) protein and an expression cassette encoding SV40 Large T antigen.

In yet another aspect, the invention relates to a use of a plasmid encoding SV40 Large T antigen for rescue of Vesicular Stomatitis Virus (VSV) in a HEK293 cell line or a HEK293 cell line adapted to suspension growth by means of transient co-transfection with at least one at least one plasmid comprising (i) an expression cassette comprising a VSV genomic cDNA and (ii) at least one expression cassette encoding VSV nucleoprotein (N) protein, VSV phosphoprotein (P) protein and VSV large (L) protein.

SHORT DESCRIPTION OF THE FIGURES

FIG. 1: Schematic overview of VSV rescue in HEK293-F cells.

Figure 2:
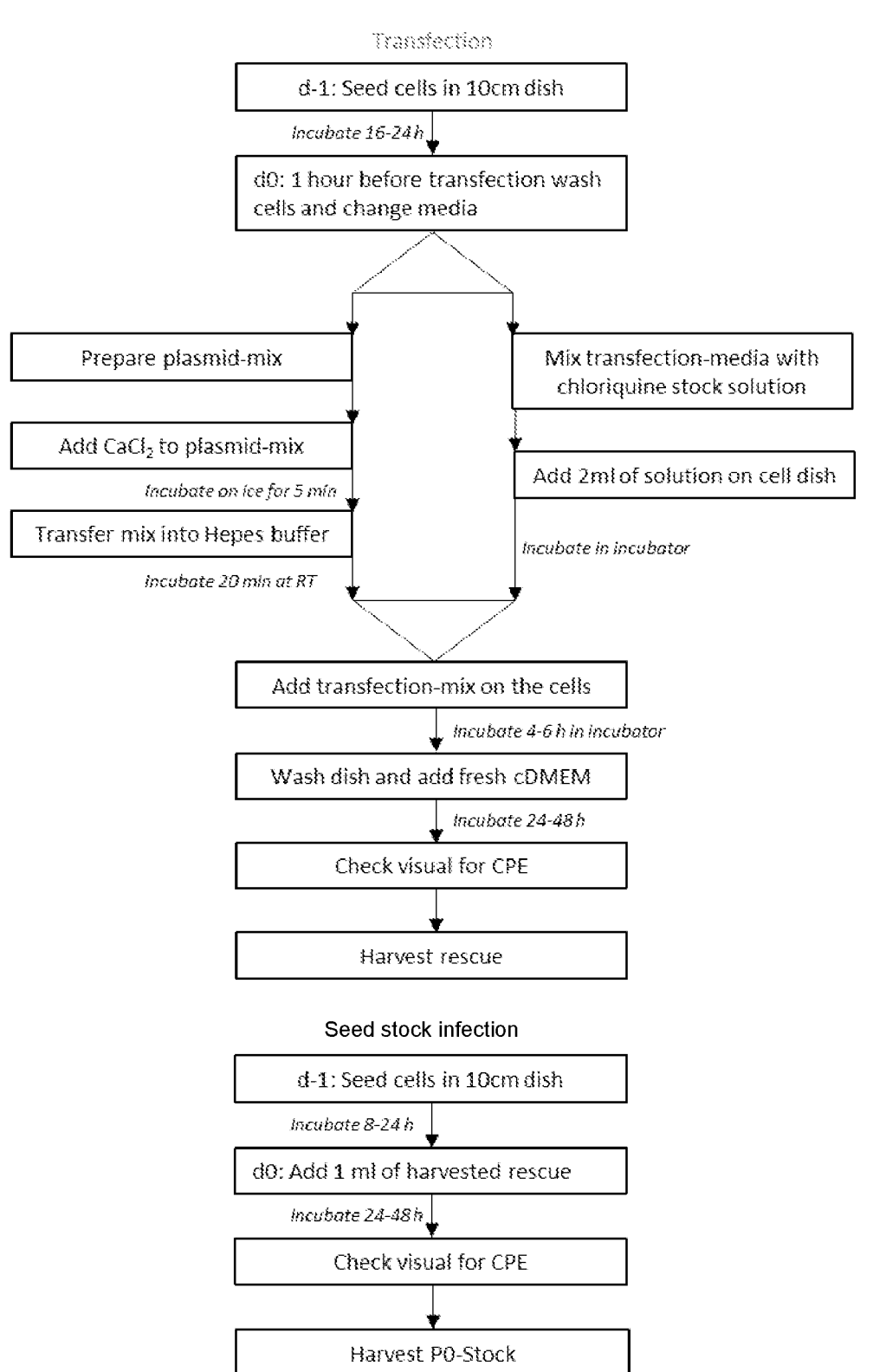

FIG. 2: Process flow-chart of VSV rescue and amplification.

Figure 3:
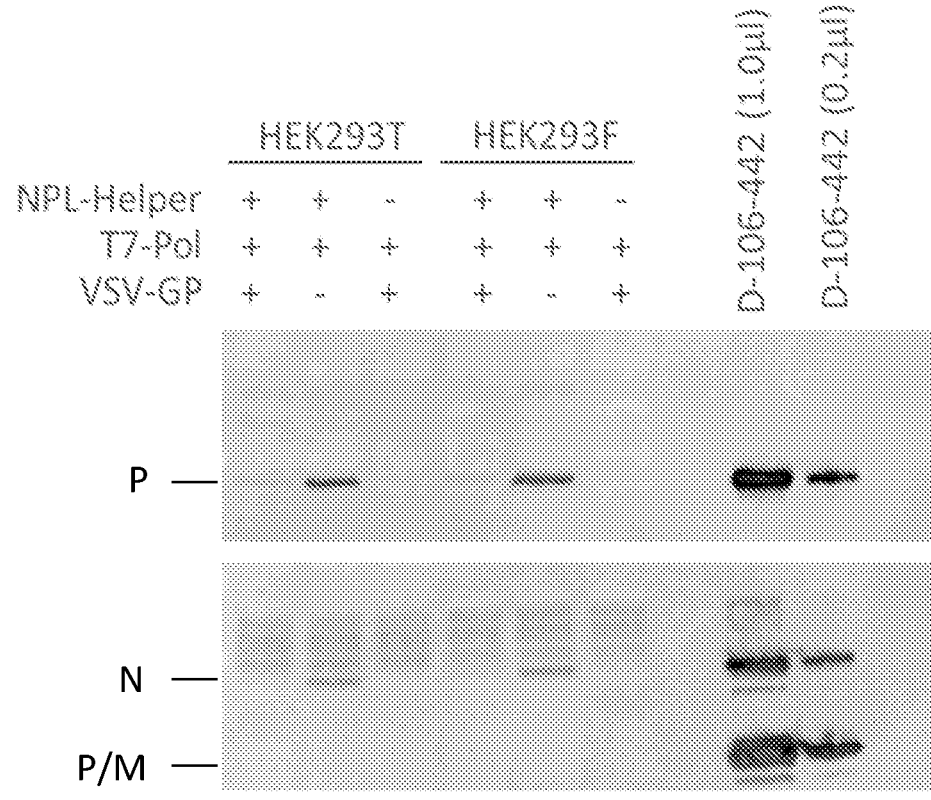

FIG. 3: Viral protein expression following transfection in HEK293T (lanes 1-3) and HEK293-F (lanes 4-6) cells in a Western Blot stained with an anti-P protein polyclonal antibody (top) or an generic serum against VSV (bottom). As positive control, a preparation of $2.36 \times 10^{10}$ TCID50/ml purified VSV-GP virions (D-106-442) is shown at 1.0 μl and 0.2 μl in lanes 7 and 9, respectively. P, N and P/M indicate the expected position of P protein, N protein and the mixed band comprising P and M protein, respectively. NPL-Helper generically refers to plasmids pCAG VSV-N, pCAG VSV-P and pCAG VSV-L, T7-Pol refers to plasmid pCAGGS T7-RNAP IRES Puro and VSV-GP refers to the plasmid comprising VSV genomic cDNA of VSV-GP.

Figure 4A:
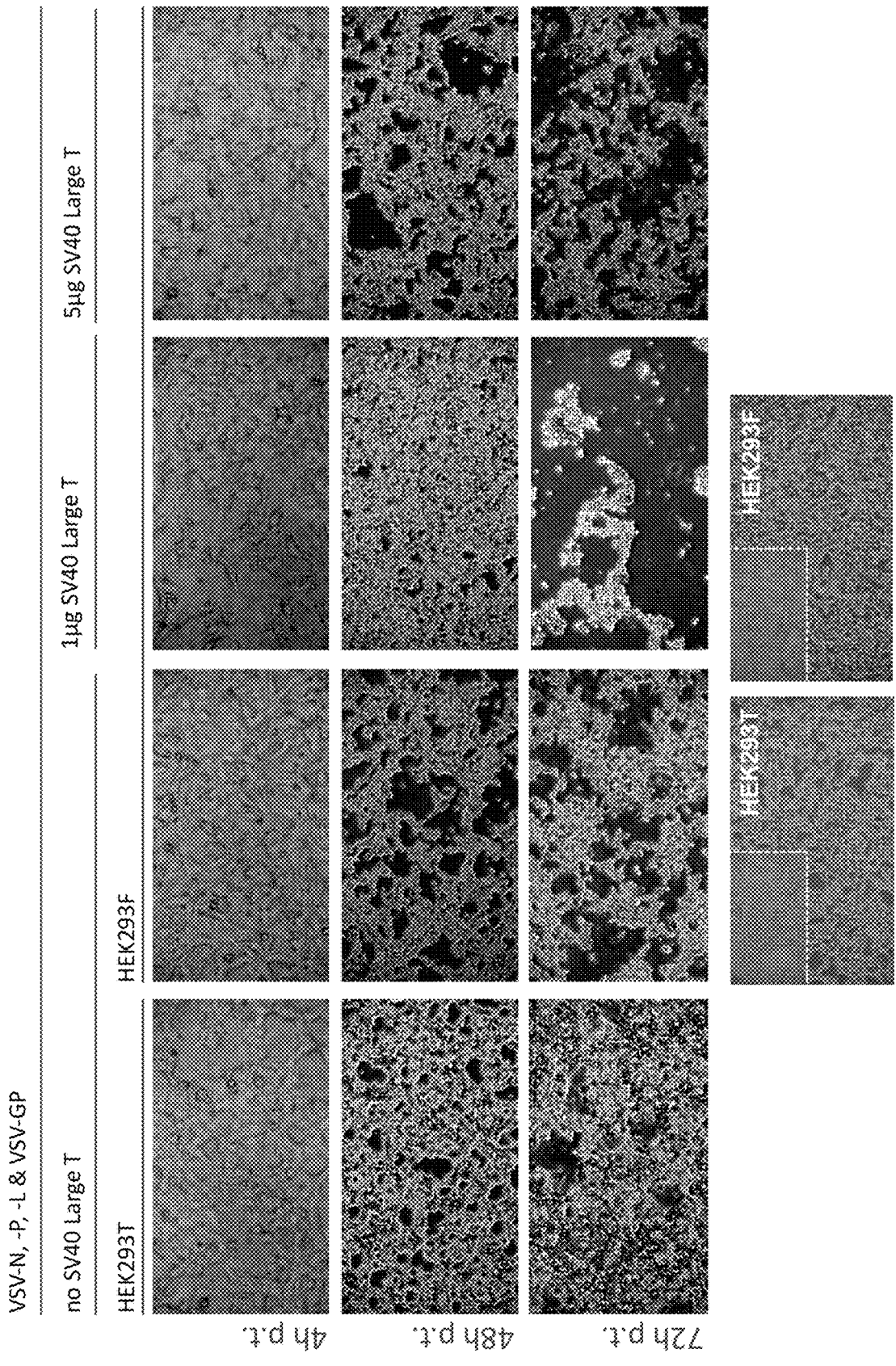
Figure 4B:
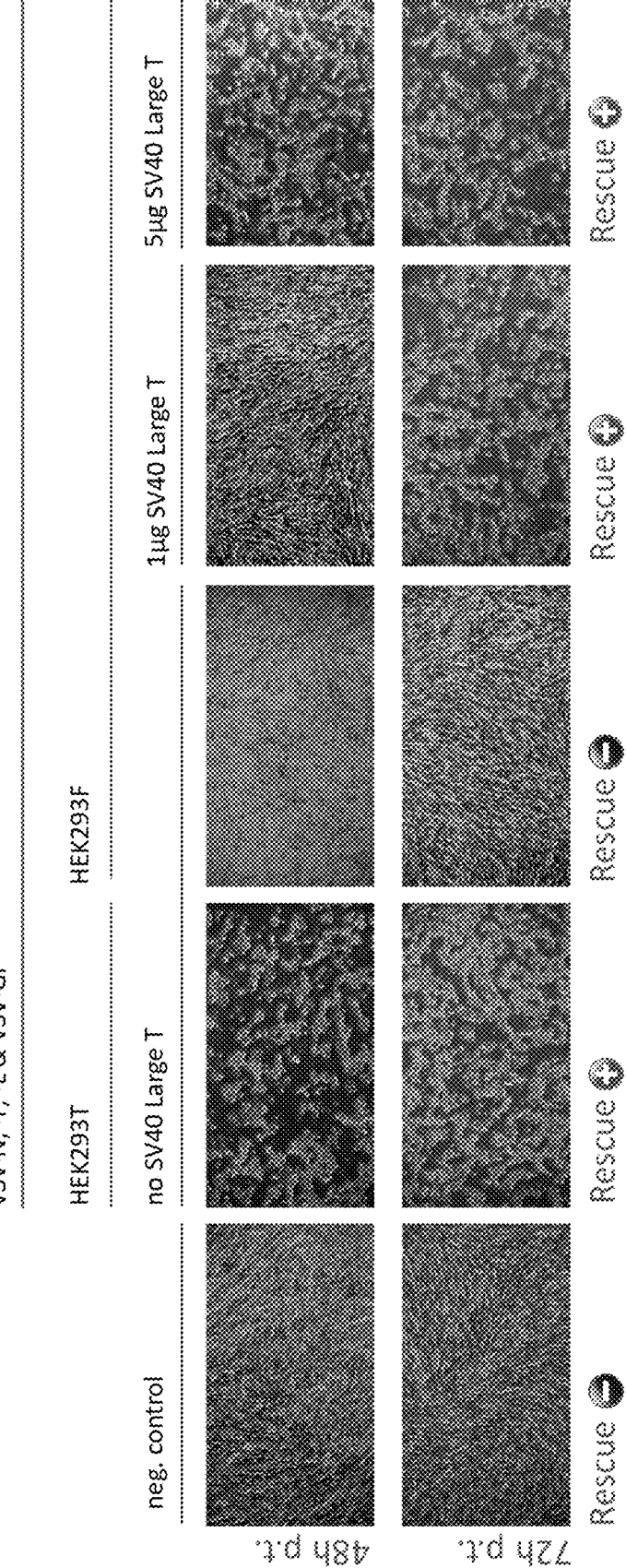

FIG. 4: Transient transfection for VSV rescue+/−transient transfection of SV40 Large T antigen in HEK293-F cells. HEK293T and HEK293-F cells were transfected with plasmids pVSV-LCMV GP (VSV-GP), pCAG VSV-N, pCAG VSV-P and pCAG VSV-L (VSVN, -P, -L) and pCAGGS T7-RNAP IRES Puro with (1 μg or 5 μg SV40 Large T) or without (no SV40 Large T) co-transfection of plasmid pCAG SV40 LargeT. (A) Representative bright-field microscopy images are shown after 4 h post-transfection (4 h p.t., top row) and representative dark-field microscopy images are shown 48 h post-transfection (48 h p.t., middle row) and 72 h post-transfection (72 h p.t., bottom row). In the bottom panel, untransfected HEK293T (left) and HEK293-F cells (right) are shown as dark-field images with bright-field images in the upper left corner for comparison. (B) Passages of harvest supernatants of the HEK293-F and HEK293T cells 48 h p.t. and 72 h p.t. were further analysed for infection on BHK21C1.13 cells. Representative dark-field microscopy images are shown 48 hours after infection with the harvest supernatants of (A) as indicated or with fresh medium as negative control (left-hand column). The symbol (−) at the bottom of a column indicates no VSV rescue and the symbol (+) at the bottom of a column indicates successful VSV rescue. A clear cytopathic effect (CPE) was visible in BHK21C1.13 cells infected with harvest supernatants 48 h p.t. and 72 h p.t. from HEK293T cells and HEK293-F cells transiently transfected with SV40 Large T antigen, while no CPE was observed following infection with harvest supernatants 48 h p.t. and 72 h p.t. from HEK293-F cells in the absence of SV40 Large T antigen.

Figure 5A:
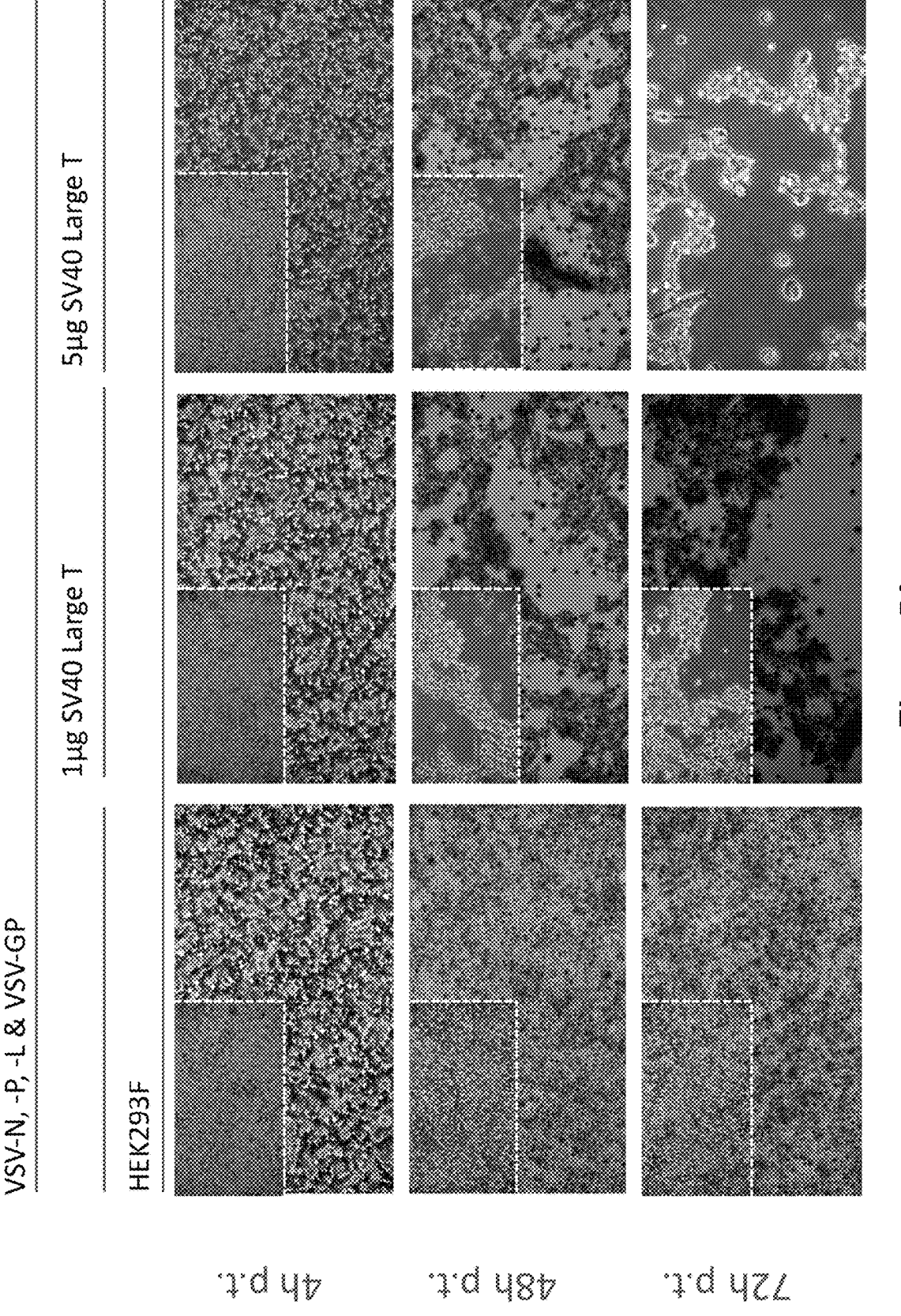

FIG. 5: Transient transfection for VSV rescue+/−transient transfection of SV40 Large T antigen in HEK293-F cells performed in an independent experiment. HEK293-F cells were transfected with plasmids pVSV-LCMV GP (VSV-GP), pCAG VSV-N, pCAG VSV-P and pCAG VSV-L (VSV-N, -P, L) and pCAGGS T7-RNAP IRES Puro with (1 μg or 5 μg SV40 Large T) or without (no SV40 Large T) co-transfection of plasmid pCAG SV40 LargeT. (A) Representative dark-field microscopy images are shown after 4 h p.t. (top row), 48 h p.t. (middle row) and 72 h p.t. (bottom) and the respective bright-filed images in the upper left-hand corner. (B) Passages of harvest supernatants of the HEK293-F cells 4 h p.t. (top row), 48 h p.t. (middle row) and 72 h p.t. (bottom) were further analysed for infection on adherent HEK293-F cells. Representative microscopy images are shown 24 hours after infection (p.i.) with the harvest supernatants 4 h p.t. (top row), 48 h p.t. (middle row) as dark-field images and with the harvest supernatants 72 h p.t. (bottom column) as bright field images. The symbol (−) at the bottom of a column indicates no VSV rescue and the symbol (+) at the bottom of a column indicates successful VSV rescue. A clear cytopathic effect (CPE) was visible in HEK293-F cells infected with harvest supernatants 48 h p.t. and 72 h p.t. from HEK293-F cells transiently transfected with 5 μg SV40 Large T antigen, while no CPE was observed following infection with harvest supernatants 48 h p.t. and 72 h p.t. from HEK293-F cells transiently transfected with 1 μg SV40 Large T antigen or in the absence of SV40 Large T antigen. Dark-field images of HEK293-F negative control cells are shown on the left-hand side.

DETAILED DESCRIPTION OF THE INVENTION

The invention relates to the rescue of Vesicular Stomatitis Virus (VSV) or genetically modified versions thereof from cDNA using transfection (e.g., CaPO$_4$-mediated transfection) of HEK293 cells or suspension adapted HEK293 cells and to the generation of virus seed stocks following virus rescue.

The general embodiments "comprising" or "comprised" encompass the more specific embodiment "consisting of". Furthermore, singular and plural forms are not used in a limiting way. As used herein, the singular forms "a", "an" and "the" designate both the singular and the plural, unless expressly stated to designate the singular only.

The term "protein" is used interchangeably with "amino acid residue sequence" or "polypeptide" and refers to polymers of amino acids of any length. These terms also include proteins that are post-translationally modified through reactions that include, but are not limited to, glycosylation, acetylation, phosphorylation, glycation or protein processing. Modifications and changes, for example amino acid sequence substitutions, deletions or insertions, can be made in the structure of a polypeptide while the molecule maintains its biological functional activity. For example, certain amino acid sequence substitutions can be made in a polypeptide or its underlying nucleic acid coding sequence and a protein can be obtained with the same properties.

The vesicular stomatitis virus (VSV) is a negative-sense single-stranded RNA (ssRNA) virus of the order Mononegavirales, which belongs together with the rabies virus to the family Rhabdoviridae. Negative-sense viral RNA is complementary to mRNA and must be converted into positive-sense RNA by an RNA-dependent RNA polymerase before translation. Thus, purified RNA of a negative-sense RNA is not infectious as it needs to be transcribed first, which requires an RNA-dependent RNA polymerase comprised in the virus particle (virion). The sequence of recombinant RNA viruses is commonly provided as cDNA sequence, as the RNA sequence is reverse transcribed for sequencing.

The negative-sense ssRNA genome of VSV contains five open reading frames coding from 3' to 5' for the N protein, P protein, M protein, G protein and L protein. The nucleoprotein (N protein) is the major component of the nucleocapsid and is required to initiate genome synthesis. The large protein (L protein) is an RNA-dependent RNA polymerase and combines with the phosphoprotein (P protein) to catalyse replication of the mRNA. The matrix protein (M protein) is associated to the inner side of the virus membrane and the glycoprotein (G protein) is a glycosylated transmembrane protein localized within the virus membrane and enables viral entry into the host cell.

The present invention relates to the rescue of vesicular stomatitis virus (VSV) from DNA in a HEK293 cell line or a HEK293 cell line adapted to suspension growth, which are typically used for large scale virus production for e.g., therapeutic applications. Although there are VSV serotypes, the VSV serotype best characterized and used in therapy is VSV Indiana (VSIV). All sequences disclosed and used herein are from VSIV. Since VSV Indiana is an RNA virus, there are several complete genome nucleotide sequences available, one example is the cDNA sequence of SEQ ID NO: 6 (GenBank accession number MH919398.1). The VSV N protein, P protein or L protein is preferably of VSIV, such as having the amino acid sequence of SEQ ID NOs: 1, 2 or 3, respectively or a sequence having at least 80%, 85%, 90% or more preferably at least 95% sequence identity thereto.

The term "VSV rescue" as used herein refers to the recovery of a negative sense RNA virus from DNA, such as plasmid DNA. The aim is to produce infectious VSV that can be used to transduce cells for analysis or large scale production. The term "infectious VSV" as used herein refers to VSV particles that infect cells susceptible to VSV infection, such as BHK or HEK293 cells or derivatives thereof. To confirm the production of infectious virus passages of harvest supernatants following transfection (e.g., 48 or 72 h post-transfection (p.t.) are added to VSV susceptible cells (seed stock infection, also referred to as PO infection) and analysed microscopically for cytopathic effects (CPE) 48 hours post-infection (p.i.).

The term "genomic RNA" as used herein refers to the heritable genetic information of an RNA virus. The person skilled in the art will understand that the genome of an RNA virus may also be provided as a DNA sequence in a vector, such as a plasmid. In the context of the present invention the VSV genome is provided as a "VSV genomic cDNA". This means it is provided as a DNA sequence in a vector, such as a plasmid. The RNA genome is then generated in a host cell following transfection of the host cell via transcription. Typically, the vector comprises an expression cassette comprising the VSV genomic cDNA under the control of a promoter and further comprising at least one terminator sequence. Moreover, the VSV genomic cDNA typically encodes the genomic, negative strand that is transcribed in-situ to VSV anti-genomic RNA ((+)-strand RNA). Preferably the VSV genomic cDNA is under the control of a T7 promoter and further comprises a T7 terminator sequence. The complementary DNA (cDNA) is DNA synthesized from a single-stranded RNA. In case of a VSV genomic cDNA, the cDNA is synthesized from the genomic RNA of VSV.

The term "gene" as used herein refers to a DNA or RNA locus of heritable genomic sequence which affects an organism's traits by being expressed as a functional product or by regulation of gene expression. Genes and polynucleotides may include introns and exons as in genomic sequence, or just the coding sequences as in cDNAs, such as an open reading frame (ORF), comprising a start codon (methionine codon) and a translation stop codon. Genes and polynucleotides can also include regions that regulate their expression, such as transcription initiation, translation and transcription termination. Thus, also included are regulatory elements such as a promoter and a terminator sequence.

The terms "nucleic acid", "nucleotide", and "polynucleotide" as used herein are used interchangeably and refer to a single or double-stranded polymer of deoxyribonucleotide bases or ribonucleotide bases read from the 5' to the 3' end and include double stranded DNA (dsDNA), single stranded DNA (ssDNA), single stranded RNA (ssRNA, negative-sense and positive-sense), double stranded RNA (dsRNA), genomic DNA, cDNA, cRNA, recombinant DNA or recombinant RNA and derivatives thereof, such as those containing modified backbones.

The term "ribonucleic acid", "RNA" or "RNA oligonucleotide" as used herein describes a molecule consisting of a sequence of nucleotides, which are built of a nucleobase a ribose sugar, and a phosphate group. RNAs are usually single stranded molecules and can exert various functions. The term ribonucleic acid specifically comprises messenger RNA (mRNA), transfer RNA (tRNA), ribosomal RNA (rRNA), short interfering RNA (siRNA), small hairpin RNA (shRNA) and micro RNA (miRNA), each of which plays a specific role in biological cells. It includes small non-coding RNAs, such as microRNAs (miRNA), short interfering RNAs (siRNA), small hairpin RNA (shRNA), and Piwi-interacting RNAs (piRNA). The term "non-coding" means that the RNA molecule is not translated into an amino acid sequence. The term "coding" means that the RNA molecule is translated into an amino acid sequence.

The term "coding strand" or "positive-sense strand" refers to a RNA strand encoding for proteins.

The term "non-coding strand" "anti-sense strand" or "negative-sense strand" or "negative-strand" refers to an RNA strand that needs to be transcribed by an RNA-dependent RNA polymerase into a positive strand RNA prior to translation.

A "vector" is a nucleic acid that can be used to introduce a heterologous polynucleotide into a cell. One type of vector is a "plasmid", which refers to a linear or circular double stranded DNA molecule into which additional nucleic acid segments can be ligated. Another type of vector (e.g., retroviruses, adenoviruses, adeno-associated viruses, VSV and MeV replication defective or active form), wherein additional DNA or RNA segments can be introduced into the viral genome. Introduction of nucleic acid is generally referred to as transfection, while introduction of nucleic acid via viral infection is generally referred to as transduction.

The term "encodes" and "codes for" refers broadly to any process whereby the information in a polymeric macromolecule is used to direct the production of a second molecule that is different from the first. The second molecule may have a chemical structure that is different from the chemical nature of the first molecule. For example, the term "encode" describes the process of semi-conservative DNA replication, where one strand of a double-stranded DNA molecule is used as a template to encode a newly synthesized complementary sister strand by a DNA-dependent DNA polymerase. Further, a DNA molecule can encode an RNA molecule (e.g., by uses a DNA-dependent RNA polymerase) or a RNA molecule (negative stranded) can encode an RNA molecule (positive-stranded) (e.g., by use of a RNA-dependent RNA polymerase). Also, an RNA molecule (positive-stranded) can encode a polypeptide, as in the process of translation. When used to describe the process of translation, the term "encode" also extends to the triplet codon that encodes an amino acid. An RNA molecule can also encode a DNA molecule, e.g., by the process of reverse transcription using an RNA-dependent DNA polymerase. When referring to a DNA molecule encoding a polypeptide, a process of transcription and translation is referred to.

The term "expression" as used herein refers to transcription and/or translation of a (heterologous) nucleic acid sequence within a host cell. The level of expression of a gene product of interest in a host cell may be determined on the basis of either the amount of the corresponding mRNA (or positive-stranded RNA) that is present in the cell, or the amount of the polypeptide encoded by the selected sequence. For example, RNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The product of interest encoded by a heterologous nucleic acid sequence may also be a non-coding RNA. The level of expression of a non-coding RNA, such as a miRNA, siRNA or shRNA, may be quantified by PCR, such as qPCR.

The term "expression cassette" as used herein refers to a distinct component of a DNA molecule responsible for RNA synthesis, comprising a sequence to be expressed and regulatory elements, typically at least a promoter and a terminator sequence. In case the final product is a protein, the sequence to be expressed comprises an open reading frame coding for the protein. According to the present invention the expression cassette encodes one or more proteins or a VSV genomic cDNA. The expression cassette is typically part of a vector, such as a plasmid or a viral vector.

The term "gene product" refers to both the mRNA polynucleotide and polypeptide that is encoded by a gene or DNA polynucleotide.

The term "HEK293 cell line" as used herein refers to an adherent human cell line that originates from human embryonic kidney and was originally immortalized in 1973 by the integration of a 4 kbp adenoviral 5 (ad5) genome fragment including the E1A and E1B genes at chromosome 19 (Graham et al., J. Gen. Virol. (1977) 36: 59-72; Malm et al., Nature research, Scientific Reports (220) 10:18996). This cell line is for example obtainable from ATCC and DSMZ (ATCC-CRL-1573; DSMZ No: ACC305; RRID: CVCL_0045). This cell line may also be referred to as parental HEK293 cell line or parental HEK293 cell lineage. The person skilled in the art would understand that the term HEK293 cell line as used herein includes subclones thereof. The term "HEK293 cell line adapted to suspension growth" refers to cell lines clonally derived from the parental HEK293 cell line that have been adapted to high-density suspension growth in serum-free medium, enabling large-scale cultivation and bioproduction of therapeutic proteins or virus in bioreactors. These include, without being limited thereto the industrially relevant suspension cell lines HEK293-F, HEK 293-H and FreeStyle HEK293-F cells. FreeStyle HEK293-F cells are adapted to suspension culture in FreeStyle™ 293 Expression medium and are e.g., obtainable from ThermoFisher (R79007; RRID:CVCL_D603). HEK293-F and HEK293-H cells were prepared by clonal selection from HEK293 cells for fast growth in serum-free medium (SFM), superior transfection efficiency and a high level of protein expression and are e.g., obtainable from ThermoFisher (HEK293-F: 11625019, RRID:CVCL_6642; HEK293-H: 11631017, RRID:CVCL_6643). The HEK293-H strain is a variant, which when grown in serum supplemented medium demonstrate better adherence in monolayer culture and ease of use for plaque assays and other anchorage dependent applications. HEK293-F and HEK-293-H are provided as adapted to Gibco® CD 293 medium. Other HEK293 cell lines adapted to suspension growth in cell culture are, without being limited thereto, e.g., HEK293.2sus (ATCC CRL-1573.3) HEK293-SF-3F6 (ATCC CRL-12585; RRID:CVCL_4 V94), Expi293F (ThermoFisher A14527/A14528/100044202 (cGMP banked); RRID:CVCL_D615) and HEK293-S (Ximbio 154155; RRID:CVCL_A784). HEK293 cell lines adapted to suspension growth may also be referred to as "293 cells, SFM adapted".

The present invention relates to a method for rescue of Vesicular Stomatitis Virus (VSV) from DNA in a HEK293 cell line or a HEK293 cell line adapted to suspension growth comprising (a) providing cells from a HEK293 cell line or a HEK293 cell line adapted to suspension growth in cell culture, (b) transfecting the cells with at least one plasmid, wherein the at least one plasmid comprises (i) an expression cassette comprising a VSV genomic cDNA; (ii) at least one expression cassette encoding VSV nucleoprotein (N) protein, VSV phosphoprotein (P) protein and VSV large (L) protein; and (iii) an expression cassette encoding SV40 Large T antigen; (c) culturing the transfected cells; and (d) harvesting the cell culture supernatant comprising the rescued VSV. The cell culture supernatant may be harvested any time following transfection, preferably it is harvested 24 h to 96 hours post-transfection, more preferably 48 h to 72 hours post transfection. The cells provided in cell culture are selected from a HEK293 cell line or a HEK293 cell line adapted to suspension growth. Preferably the cells provided in a cell culture are a HEK293 cell line adapted to suspension growth. A HEK293 cell line may be any parental HEK293 cell line that has been adapted to efficiently grow in suspension, typically in the absence of serum, and maintaining the ability for high virus production (such as cell specific productivity) comparable to the parental HEK293 cell line. Suitable HEK293 cell lines adapted to suspension growth are without being limited thereto HEK293-F cells, HEK293-H cells, FreeStyle HEK293-F cells, HEK293-SF-3F6 cells, Expi293F cells, HEK293.2sus cells and HEK293-S cells. Preferred HEK293 cell lines adapted to suspension growth in the context of the present invention are HEK293-F cells, HEK293-H cells, FreeStyle HEK293-F cells, and Expi293F cells, more preferably HEK293-F cells or Expi293F cells, even more preferably HEK293-F cells. In preferred embodiments the harvested cell culture supernatant comprises infectious VSV. Infectious particles may be determined by adding said harvested cell culture supernatant to cells susceptible to VSV infection, such as BHK or HEK293 cells or derivatives thereof. Cells susceptible to VSV infection include the HEK293 cell line and the HEK293 cell lines adapted to suspension growth described herein as well as other HEK293 derivatives, including without being limited thereto HEK293T cells and HEK293E cells. Suitable BHK cells include without being limited thereto BHK-21C1.13 cells (ATCC CCL-10; RRID: CVCL_1915). Infectious virus is detected microscopically for cytopathic effects (CPE) about 48 hours post-infection. Thus, in certain embodiments infectious particles are determined by the passage of virions, wherein (i) the harvested cell culture supernatant is added to cells susceptible to VSV infection, preferably BHK21, such as BHK-21C1.13 cells or HEK293-F cells and (ii) infectious virus is detected microscopically for cytopathic effects 48 hours post-infection.

The expression cassette comprising a VSV genomic cDNA encodes the VSV genome, typically in an anti-sense orientation, and further comprises a promoter and a terminator sequence. The at least one expression cassette encoding VSV nucleoprotein (N) protein, VSV phosphoprotein (P) protein and VSV large (L) protein comprises a sequence encoding VSV N protein, P protein and/or L protein and further a promoter and a terminator sequence. The term "at least one expression cassette" as used herein indicates that the N protein, VSV P protein and L protein may be encoded by a sequence within the same expression cassette or by separate expression cassettes or a combination thereof. In cases where more than one protein are encoded by an expression cassette the sequences encoding the more than one proteins are linked by a sequence that allows for translation initiation in a cap-independent manner, such as an internal ribosomal entry site (IRES). Moreover, where the N protein, P protein or L protein are encoded by separate, i.e., three expression cassettes, or at least by more than one expression cassette, the expression cassettes may be on the same plasmid and/or on separate plasmids. The expression cassette encoding SV40 Large T antigen comprises a sequence encoding the SV40 Large T antigen and a promoter and a terminator sequence. The at least one plasmid comprising the (i) expression cassette comprising the VSV genomic cDNA, the (ii) at least one expression cassette encoding the N protein, the P protein and the L protein and the (iii) expression cassette comprising the SV40 Large T antigen may be on 1, 2, 3, 4 or 5 plasmids. Preferably the expression cassette (i), the at least one expression cassette (ii) and the expression cassette (iii) are on separate plasmids. More preferably the at least one expression cassette (ii) are at least 3 expression cassettes, a first expression cassette encoding the N protein, a second expression cassette encoding the P protein and a third expression cassette encoding the L protein. The first, the second and the third expression cassette may be on one plasmid or on three separate plasmids or on two plasmids with one plasmid comprising two and the other plasmid comprising one of said expression cassettes. The separate plasmids may be derived from the same or different plasmids.

In certain embodiments the N protein, the P protein and the L protein are from VSV Indiana (VSIV). In certain preferred embodiments the N protein has the amino acid sequence of SEQ ID NO: 1 or a sequence having at least 95% sequence identity thereto, the P protein has the amino acid sequence of SEQ ID NO: 2 or a sequence having at least 95% sequence identity thereto and/or the L protein has the amino acid sequence of SEQ ID NO: 3 or a sequence having at least 95% sequence identity thereto. The person skilled in the art would understand that the protein having at least 95% sequence identity with the recited sequence of a specific protein are functional homologous of the specific protein. For examples the N protein comprising a sequence having at least 95% sequence identity with the amino acid sequence of SEQ ID NO: 1 is a functional homologue of the N protein having an amino acid sequence of SEQ ID NO: 1. Thus, the homologous protein further displays the same or a similar protein activity as the original sequence.

In certain embodiments, the method according to the invention further comprises a step (e) comprising transducing cells from a HEK293 cell line or a HEK293 cell line adapted to suspension growth in suspension with VSV obtained in step (d); and optionally a step (f) comprising producing VSV in the cells of step (e) in suspension culture at large scale, preferably at >50 L. Preferably the HEK293 cell line or HEK293 cell line adapted to suspension growth according to step (e) is the same as cell line as the HEK293 cell line or HEK293 cell line adapted to suspension growth according to step (a). Although VSV can be produced in adherent HEK293 cells, virus production is typically more efficient in suspension due to higher cell density during culture, particularly at large scale and further allows for virus production in the absence of serum. Preferably the HEK293 cell line or HEK293 cell line adapted to suspension growth according to step (e) and step (a) is selected from the group consisting of HEK293-F cells, HEK293-H cells, FreeStyle HEK293-F cells, and Expi293F cells, more preferably the HEK293 cell line or HEK293 cell line adapted to suspension growth according to step (e) and step (a) is HEK293-F cells or Expi293F cells, even more preferably HEK293-F cells. The term "large scale" as used herein refers to a culture volume of more than 5 L, preferably more than 10 L, more preferably 25 L and even more preferably more than 50 L.

Transfection may be performed in adherent cells or in suspension, but is typically performed in adherent cells due to higher transfection efficiency. In certain embodiments the cells in step (a) are provided, transfected and cultured as adherent cells. HEK293 cell lines adapted to suspension growth may be rendered adherent by addition of fetal calf serum (FCS) in a range of 1-12%, preferably 3-10%, more preferably 5-10% (v/v) of the culture medium. Typically, transient transfection is more efficient in adherent cells compared to suspension cells. In certain embodiments the cells are transiently transfected in step (b), preferably the adherent cells are transiently transfected in step (b). Transfecting the cells in step (b) may comprises the use of a chemical-based transfection agent, such as lipofection (lipid transfection), polyethylenimine (PEI), DEAE dextran or calcium phosphate transfection, preferably calcium phosphate transfection. Wherein the cells are preferably transiently transfected using the chemical-based transfection agent, more preferably the adherent cells are transiently transfected using the chemical-based transfection agent.

In certain embodiments the cells in step (b) are further transfected or transduced with a plasmid or a helper virus comprising an expression cassette encoding bacteriophage T7 RNA polymerase under the control of an RNA polymerase II-dependent promoter, and the expression cassette comprising the VSV genomic cDNA comprises the VSV genomic cDNA under the control of a T7 promoter and a T7 terminator sequence; and optionally the at least one expression cassette encoding VSV N protein, VSV P protein and VSV L protein comprises the sequence encoding the VSV N, P and/or L protein under the control of a promoter and a terminator sequence. The RNA polymerase II-dependent promoter in the expression cassette encoding the bacteriophage T7 RNA polymerase is preferably a strong promoter, such as a CMV promoter or a CAG promoter. The CAG promoter comprises the cytomegalovirus (CMV) early enhancer element (C), the promoter, the first exon and the first intron of the chicken beta-actin gene (A) and the splice acceptor of the rabbit beta-globin gene (G) (Niwa H et al., (1991) Gene 108(2): 193-9). The term "a T7 terminator sequence" may also comprise more than one T7 terminator sequences, such as two or three T7 terminator sequences, preferably two T7 terminator sequences. The expression cassette further comprises a terminator sequence and optionally a marker gene separated by an IRES sequence. A typical helper virus used for expression of bacteriophage T7 RNA polymerase is, without being limited thereto, e.g., a vaccinia virus. In a preferred embodiment the method is a helper-virus free method, wherein the cells in step (b) are transfected with the plasmid comprising an expression cassette encoding bacteriophage T7 RNA polymerase under the control of an RNA polymerase II-dependent promoter. In certain embodiments the bacteriophage T7 RNA polymerase has the amino acid sequence of SEQ ID NO: 4 or has at least 95% sequence identity with the amino acid sequence or SEQ ID NO: 4. In certain alternative or additional embodiments the nucleotide sequence encoding the bacteriophage T7 RNA polymerase is codon-optimized.

The at least one expression cassette encoding the VSV N protein, VSV P protein and VSV L protein may be transfected as one or more helper plasmids. For example, the one or more helper plasmid comprises (i) a first helper plasmid comprising an expression cassette comprising a sequence encoding the VSV N protein, preferably comprising a sequence encoding the VSV N protein under the control of a promoter and a terminator sequence; (ii) a second helper plasmid comprising an expression cassette comprising a sequence encoding the VSV P protein, preferably comprising a sequence encoding the VSV P protein under the control of a promoter and a terminator sequence; and (iii) a third helper plasmid comprising an expression cassette comprising a sequence encoding the VSV L protein, preferably comprising a sequence encoding the VSV L protein under the control of a promoter and a terminator sequence and (iv) optionally at least one further helper plasmid comprising an expression cassette comprising a sequence encoding a VSV glycoprotein (G) and/or an expression cassette comprising a sequence encoding a VSV matrix (M) protein, preferably under the control of a promoter and a terminator sequence. Suitable promoter for an expression cassette comprising a sequence encoding VSV-N, —P, -L, G and/or M are strong promoter, preferably strong RNA polymerase II-dependent promoter, such as CMV or CAG.

The expression cassette encoding SV40 Large T antigen according to the method of the invention is transfected as a plasmid comprising said expression cassette encoding SV40 Large T antigen. The expression cassette comprises the sequence encoding the SV40 Large T antigen under the control of a promoter and further comprises a terminator sequence, preferably under the control of a strong RNA polymerase II-dependent promoter, more preferably a CMV promoter or a CAG promoter. In certain embodiments the SV40 large T antigen encoded by the expression cassette in the method according to the invention has the amino acid sequence of SEQ ID NO: 5 or has at least 95% sequence identity with the amino acid sequence of SEQ ID NO: 5. Thus, in certain embodiments the expression cassette comprises a nucleic acid sequence encoding the SV40 large T antigen having an amino acid sequence of SEQ ID NO: 5 or having at least 95% sequence identity with the amino acid sequence of SEQ ID NO: 5.

The HEK293 cell line or HEK293 cell line adapted to suspension growth without being limited thereto may be selected from the group consisting of HEK293, HEK293-F, HEK-293-H, Expi293F and Freestyle HEK293-F. Preferably the cells are from a HEK293 cell line adapted to suspension growth, more preferably the cells are from a HEK293 cell line adapted to suspension growth selected from the group consisting of HEK293-F, HEK-293-H, Expi293F and Freestyle HEK293-F. Even more preferably, the HEK293 cell line adapted to suspension growth are HEK293-F cells. The advantage of using HEK293 and particularly a HEK293 cell line adapted to suspension growth is that the same cell line can be used for VSV rescue from VSV genomic cDNA (typically performed using adherent cells) and for the production of VSV in suspension cell culture. This allows the entire process for production to be performed in a single cell line, which simplifies regulatory approval.

The VSV genomic cDNA according to the method of the invention is a viral full-length genomic cDNA or a modified viral genomic cDNA. Viral full-length genomic cDNA provides wild-type virus such as VSV Indiana. The VSV genomic cDNA may also be a modified viral genomic cDNA. For example, the glycoprotein (G) may be replaced with the glycoprotein from a different (heterologous) virus, such as with the glycoprotein of the Lymphocytic Choriomeningitis Virus (LCMV). Replacing the glycoprotein may alter the virus' tropism as well as other characteristics of the virus, such as avoiding neural inflammation associated with the wild-type virus or its immunogenicity. VSV comprising the glycoprotein of LCMV may also be referred to as VSV-GP. In certain embodiments the VSV genomic cDNA according to the method of the invention is a modified viral genomic cDNA (modified VSV genomic cDNA). A modified VSV genomic cDNA comprises without being limited thereto a VSV genomic cDNA wherein the gene encoding the G protein is replaced with another viral receptor, such as the glycoprotein GP of the Lymphocytic Choriomeningitis Virus (LCMV), the GP protein of the Dandenong virus (DANDV) or Mopeia virus (MOPV) (as described in more detail in WO 2020/104694), or the GP protein of the arenavirus. In a preferred embodiment the glycoprotein G in the VSV genomic cDNA is replaced with the glycoprotein GP of the Lymphocytic Choriomeningitis Virus (LCMV), preferably from the strain WE-HPI. Such VSV is for example described in WO2010/040526 and named VSV-GP. The glycoprotein GP of the Lymphocytic Choriomeningitis Virus (LCMV) may be GP1 or GP2 but may also include glycoproteins from different LCMV strains. In particular, LCMV-GP can be derived from LCMV wild-type or LCMV strains LCMV-WE, LCMV-WE-HPI, LCMV-WE-HPI opt. In a preferred embodiment, the gene coding for the glycoprotein GP of the LCMV encodes for a protein with an amino acid sequence as shown in SEQ ID NO:7 or an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:7 while the functional properties of the VSV comprising the glycoprotein GP encoding an amino acid sequence as shown in SEQ ID NO:7 are maintained.

Moreover, modified viral genomic cDNA may comprise additional genes, e.g., in an intergenic locus of the genomic cDNA. The additional gene is preferably a heterologous gene encoding a heterologous protein. Thus, in one embodiment the VSV genomic cDNA further encodes at least one heterologous protein, such as a therapeutic protein, and antigen, such as a tumor-specific or tumor associated antigen or a reporter gene.

The term "heterologous polypeptide" or "heterologous protein" as used herein refers to a protein derived from a different organism or a different species from the recipient, i.e., the RNA virus, such as VSV. In the context of the present invention the skilled person would understand that it refers to a protein not naturally expressed by VSV. The term "heterologous" when used with reference to portions of a protein may also indicate that the protein comprises two or more amino acid sequences that are not found in the same relationship to each other in nature. In the context of the present invention it is typically a therapeutic protein, an antigen, such as a tumor-specific or tumor-associated antigen, or a reporter (such as luciferase or a fluorescent protein). A heterologous polypeptide is encoded by a heterologous nucleic acid sequence or gene.

The term "therapeutic protein" refers to proteins that can be used in medical treatment of humans and/or animals. These include, but are not limited to antibodies, growth factors, blood coagulation factors, cytokines, such as interferons and interleukins, chemokines and hormones, preferably, growth factors, cytokines, chemokines and antibodies.

The term "cytokine" refers to small proteins, which are released by cells and act as intercellular mediators, for example influencing the behavior of the cells surrounding the secreting cell. Cytokines may be secreted by immune cells or other cells, such as T-cells, B-cells, NK cells and macrophages. Cytokines may be involved in intercellular signaling events, such as autocrine signaling, paracrine signaling and endocrine signaling. They may mediate a range of biological processes including, but not limited to immunity, inflammation, and hematopoiesis. Cytokines may be chemokines, interferons, interleukins, lymphokines or tumor necrosis factors.

As used herein, "growth factor" refers to proteins or polypeptides that are capable of stimulating cell growth.

As used herein, a "reporter gene" is a polynucleotide encoding a reporter protein or "reporter" that can be easily detected and quantified. Thus, a measurement of the level of expression of the reporter is typically indicative of the level of transcription and/or translation. The gene encoding the reporter is a reporter gene. For example, a reporter gene can encode a reporter, for example, an enzyme whose activity can be quantified, for example, alkaline phosphatase (AP) (such as secreted embryonic alkaline phosphatase), chloramphenicol acetyltransferase (CAT), Renilla, Gaussia or Firefly luciferase protein(s). Reporters also include fluorescent proteins, for example, green fluorescent protein (GFP) or any of the recombinant variants of GFP, including enhanced GFP (EGFP), blue fluorescent proteins (BFP and other derivatives), cyan fluorescent protein (CFP and other derivatives), yellow fluorescent protein (YFP and other derivatives) and red fluorescent protein (RFP and other derivatives) or other fluorescent proteins, such as mCherry and mWasabi.

The term heterologous refers to the RNA virus rather than the host or patient infected with the virus and therefore explicitly encompasses eukaryotic, particularly human proteins. The heterologous protein is a protein derived from a different organism or a different species from the recipient, i.e., the RNA virus VSV. The at least one heterologous protein encoded by the RNA virus according to the invention may be a therapeutic protein, a reporter or a tumor antigen. Preferably the at least one heterologous protein is a therapeutic protein with immune-modulatory or cell death modulatory function, preferably selected from the group consisting of cytokines, chemokines, growth factors and antibodies. The therapeutic protein may be also a membrane bound protein or may be rendered membrane bound by fusing a transmembrane domain, such as the transmembrane domain of CD4, to the heterologous protein, preferably linked via a linker. The therapeutic protein may also be an encoded suicide gene. Alternatively or in addition the at least one heterologous protein is a tumor antigen (including a tumor-specific and/or tumor-associated antigen), such as lineage antigens, neoantigens, testis antigens and oncoviral antigens. The term "tumor-specific antigen" refers to an antigen exclusively expressed in the tumor cell but not in any other tissue of the organism. The term "tumor-associated antigen" refers to an antigen overexpressed in the tumor cell compared to other tissue in the organism, i.e., expressed at a higher level. The tumor antigen may also be a neoantigen or neoantigens. Wherein neoantigens are newly formed antigens arising from tumor somatic mutations. The person skilled in the art would know how to detect and determine neoantigens from a patient. In another embodiment the heterologous protein is a reporter protein, such as green florescent protein, red florescent protein, mCherry or mWasabi. Particularly for therapeutic purposes, the heterologous protein is preferably a therapeutic protein with immune-modulatory or cell death modulatory function or a tumor antigen.

The person skilled in the art will understand that while the method of the present invention is exemplified for rescue of Vesicular Stomatitis Virus (VSV) from DNA in a HEK293 cell line or a HEK293 cell line adapted to suspension growth, it can be easily adapted to other negative-stranded RNA viruses, such as of the order of Mononegavirales, Orthomyxoviridae, Bunyaviridae and/or Arenaviridae, particularly Mononegavirales. Thus, in another aspect, the method for rescue of a negative-stranded RNA virus comprising (a) providing cells from a HEK293 cell line or a HEK293 cell line adapted to suspension growth in cell culture, (b) transfecting the cells with at least one plasmid, wherein the at least one plasmid comprises (i) an expression cassette comprising a negative-stranded RNA virus genomic cDNA; (ii) at least one expression cassette encoding proteins of the negative-stranded RNA virus, such as proteins of the nucleocapsid, (e.g., nucleoprotein (N/NP) protein, phosphoprotein (P) protein and large (L) protein for Mononegavirales, particularly Rhabdoviridae, Paramyxoviridae, Filoviridae and Bornaviridae); and (iii) an expression cassette encoding SV40 Large T antigen; (c) culturing the transfected cells; and (d) harvesting the cell culture supernatant comprising the rescued negative stranded RNA virus. In preferred embodiments the harvested cell culture supernatant comprises infectious negative-stranded RNA virus. The further embodiments and aspects exemplified for VSV herein also apply to other negative-stranded RNA viruses.

In another aspect the invention relate to a use of a HEK293 cell line or a HEK293 cell line adapted to suspension growth for rescue of Vesicular Stomatitis Virus (VSV) by means of transient transfection of at least one plasmid comprising (i) an expression cassette comprising a VSV genomic cDNA, and (ii) at least one expression cassette encoding VSV nucleoprotein (N) protein, VSV phosphoprotein (P) protein and VSV large (L) protein and an expression cassette encoding SV40 Large T antigen. The embodiments and detailed description with regard to the method according to the invention similarly apply to the use of a HEK293 cell line or a HEK293 cell line adapted to suspension growth for rescue of Vesicular Stomatitis Virus (VSV) according to the invention. Thus, the invention also relates to a use of a HEK293 cell line or a HEK293 cell line adapted to suspension growth in a method for rescue of Vesicular Stomatitis Virus (VSV) from DNA according to the invention. In a particular embodiment of the use of a HEK293 cell line or a HEK293 cell line adapted to suspension growth according to the invention, the HEK293 cell line or HEK293 cell line adapted to suspension growth is a HEK293 cell line adapted to suspension growth, preferably selected from the group consisting of HEK293-F, HEK-293-H, Expi293F and Freestyle HEK293-F, more preferably, the HEK293 cell line adapted to suspension growth are HEK293-F cells.

In yet another aspect, the invention relates to a use of a plasmid encoding SV40 Large T antigen for rescue of Vesicular Stomatitis Virus (VSV) in a HEK293 cell line or a HEK293 cell line adapted to suspension growth by means of transient co-transfection with at least one at least one plasmid comprising (i) an expression cassette comprising a VSV genomic cDNA and (ii) at least one expression cassette encoding VSV nucleoprotein (N) protein, VSV phosphoprotein (P) protein and VSV large (L) protein. The embodiments and detailed description with regard to the method according to the invention similarly apply to the use of a plasmid encoding SV40 Large T antigen for rescue of Vesicular Stomatitis Virus (VSV) in a HEK293 cell line or a HEK293 cell line adapted to suspension growth according to the invention. Thus, the invention also relates to a use of a plasmid encoding SV40 Large T antigen in a method for rescue of Vesicular Stomatitis Virus (VSV) from DNA according to the invention. In a particular embodiment of the use of a plasmid encoding SV40 Large T according to the invention, the HEK293 cell line or HEK293 cell line adapted to suspension growth is a HEK293 cell line adapted to suspension growth, preferably selected from the group consisting of HEK293-F, HEK-293-H, Expi293F and Freestyle HEK293-F, more preferably, the HEK293 cell line adapted to suspension growth are HEK293-F cells.

EXAMPLES

For helper-virus-free VSV rescue from plasmids using transient transfection cells were transfected with at least 5 plasmids, an RNA Polymerase II-dependent vector encoding the bacteriophage T7 RNA polymerase, three separate plasmids encoding the viral proteins N, P or L under the control of a CAG promoter (pCAG VSV-N, pCAG VSV-P and pCAG VSV-L plasmid) and a plasmid encoding a cDNA clone of recombinant vesicular stomatitis virus, in which the coding sequence of the VSV glycoprotein G is exchanged by LCMV-GP. The virus genome could be transcribed from the plasmid by the bacteriophage T7 RNA polymerase to yield a full length positive-strand RNA complementary to the VSV genome. The resulting virus generated from the cDNA is referred to as VSV-LCMV-GP. A schematic drawing of the process is demonstrated in FIG. 1. T7 RNA Polymerase transcribes the DNA encoding the VSV genome into viral RNA with sense-strand orientation. Expression of this RNA in cells also expressing the nucleoprotein N and the two polymerase subunits P and L resulted in production of VSV ribonucleoproteins that are subsequently packaged into VSV-LCMV-GP virions and released from the cells by budding.

Material

Kits

Calcium Phosphate Transfection Kit

Kit Contains:

5 ml 2.5M $CaCl_2$ 25 ml 2×HEPES Buffered Saline 25 ml molecular biology grade water Chemicals, Media and Buffer Chloroquine diphosphate salt DMEM complete (cDMEM):

500 ml DMEM (Dulbecco's Modified Eagle's Medium (DMEM), high glucose, no glutamine 50 ml Fetal bovine serum (FBS), heat-inactivated 10 ml CTS™ Glutamine™-I Supplement TrypLE™ Select Enzyme (1×), no phenol red, PBS—1× w/o Ca, Mg Plasmids, animal component free and QC-tested:

1. pCAG VSV-N plasmid
2. pCAG VSV-P plasmid
3. pCAG VSV-M plasmid (optional)
4. pCAG VSV-G plasmid (optional)
5. pCAG VSV-L plasmid comprising
6. pCAG SV40 LargeT
7. pCAGGS T7-RNAP IRES Puro
8. pVSV-LCMV GP (viral cDNA, also referred to as "VSV-GP")

Helper plasmids pCAG VSV-N, pCAG VSV-P and pCAG VSV-L encode for viral trans-acting proteins required for RNP assembly, transcription and replication including N protein (SEQ ID NO: 1), P protein (SEQ ID NO: 2) and L protein (SEQ ID NO: 3). Additional expression of matrix (M) protein and viral glycoprotein (G) protein may further enhance virus rescue. Plasmids pCAG VSV-N, pCAG VSV-P, pCAG VSV-M, pCAG VSV-G, pCAG VSV-L and pCAG SV40 Large T were generated from a pSF-CAG_AMP background vector (Sigma-Aldrich, Cat. No: OGS504) comprising an ampicillin resistance gene and encode the VSV-N, -P, -M, -G, -L protein under the control of a CAG promoter. The VSV N, P, M, G and L were derived from Indiana serotype genomic cDNA clone (Lawson et al., 1995). A Kozak consensus sequence was included 5' of the initiator codon to provide an optimal sequence context for translation. The RNA Pol II-dependent vector pCAGGS T7-RNAP IRES puro was originally derived from a pCAGGS background vector (Niwa H et al., (1991) Gene 108(2): 193-9) and comprises an ampicillin resistance gene, an SV40 ori and an pBR322 ori and encodes a codon-optimized T7 polymerase (SEQ ID NO: 4) under the control of a CAG promoter and linked via an IRES sequence to a puromycine encoding sequence. Plasmid pVSV-LCMV GP encodes full-length viral genomic cDNA with the gene encoding the G protein being replaced by the gene encoding the GP protein from Lymphocytic Choriomeningitis Virus (LCMV) (SEQ ID NO: 7) to generate VSV-GP. The SV40 large T antigen (SEQ ID NO: 5) is under the control of a CMV promoter. The T7 RNAP promoter at the 5' end directs synthesis of a positive-sense genomic transcript before transcription is terminated by phage T7 terminator sequences, the plasmid comprises a pBR322 ori and a ampicillin resistance gene.

Transfection Medium 500 ml DMEM (Dulbecco's Modified Eagle's Medium (DMEM), high glucose, no glutamine 10 ml CTS™ Glutamine™-I Supplement Samples and Cell Lines HEK293-F (ThermoFisher, Cat. No.: 11625-019)

HEK293T (provided by EUFETS GmbH/BioNTech IMFS)

BHK21Cl.13 (Cell line services (CLS) Cat. No.:603126)

Generation of Adherent HEK293-F Cell Cultures

For virus recovery HEK293-F suspension cell cultures were transformed to adherent cultures at least one passage before transfection. Suspension HEK293-F cells were transformed by changing the cell culture conditions from Balanced CD® HEK293 media (FujiFilm) to fully supplemented cDMEM (10% FCS, 2% CTS™ Glutamine™-I Supplement). Cells were counted using a Nucleo counter NC-200 device (Chemometec) and seeded at $2.0\times10^6$ cells per T175 cell culture flask cells in 30 ml cDMEM. Cells were cultivated for 2-3 days at 37° C., 6% $CO_2$ and 95% humidity. Adherent HEK293-F cells are not only needed for transient transfection, but more importantly for subsequent plaque purification to obtain clonal virus.

Transfection of HEK293-F or HEK293T Cells with Plasmid DNA

Cells were seeded at $5\times10^6$ HEK293-F or HEK293T cells in a 10 cm dish in 10 ml cDMEM one day before transfection (d-1) and cultivated for 16-24 hours in the incubator at 37° C. Cells were 80% confluent at day of transfection.

At the day of transfection (d0) plasmids were mixed at the following amounts per 10 cm dish:

| | |
|---|---|
| 10.0 µg | viral cDNA (e.g., pVSV-LCMV GP) |
| 2.4 µg | pCAG VSV-N plasmid |
| 1.8 µg | pCAG VSV-P plasmid |
| 0.6 µg | pCAG VSV-L plasmid |
| 10.0 µg | pCAGGS T7-RNAP IRES Puro |
| 1.0-5.0 µg | pCAG SV40 LargeT (optional) |

Although not added in the present experiments, plasmids pCAG VSV-M and pCAG VSV-G may be added at 1 µg each to the mixture.

1 hour prior to transfection cells were carefully washed with 5 ml pre-warmed transfection medium (DMEM with Glutamine) and 8 ml pre-warmed transfection-media were carefully added to the cells without disturbing the cell layer and incubated for 1 hour in the incubator. Meanwhile the DNA master mix was prepared for transfection with the calcium-phosphate precipitation method in a 1.5 ml reaction tube comprising and mixed by snipping the tube, followed by quick spin down.

For each rescue a tube was prepared comprising sterile, cell culture grade $H_2O$ to provide a total final volume of at least 450 µl volume (with the DNA-mixture). The specific amount of viral cDNA and/or pCAG SV40 LargeT was added to the respective tube and mixed by pipetting up and down and further the DNA-mastermix was added and mixed by snipping the tube and quick spin. 50.0 µl of 2.5 M $CaCl_2$ (kept on ice until use) were added in each tube and mixed by pipetting up and down and the DNA/$CaCl_2$ mixture was incubated for exactly 5 minutes at 4° C.

For each rescue 500 μl 2×HEPES buffer (Sigma) was pipetted into a 15 ml reaction tube, placed on a vortex mixer and the DNA/CaCl$_2$ mixture was added slowly and dropwise under vigorous vortexing for about 30 seconds, using a 1000 μl microliter pipette and vortex for another 30 seconds. The mixture was incubated at room temperature for a total of 20 minutes to allow the formation of calcium-phosphate-DNA precipitates, without further mixing.

2 ml transfection medium were mixed with 10 μl of a 25 mM chloroquine stock solution and carefully added using a serological pipette to the 10 cm tissue culture dish with 80% confluent cells. The dish was gently moved to mix (total volume in the dish: 10 ml, final concentration 25 μM chloroquine) and the cells were placed back into the incubator for the rest of the 20 minutes incubation. The transfection mix was added drop-wise with a 1000 μl microliter pipette to different areas of the cell layer and the dish was gently moved for even distribution of the calcium-phosphate-DNA complexes. Cells were incubated in the incubator at 37° C. and medium comprising chloroquine was exchanged after 4 hours with 10 ml prewarmed cDMEM after washing the cells once with 5 ml cDMEM and cultured as indicated. 50% of media was replaced if necessary every two days to prevent the media becoming acidic.

Harvest of Rescue

At the indicated timepoint post-transfection the supernatant of the 10 cm dishes was harvested and transferred into a 15 ml tube. The tubes were centrifuged for 4 minutes at 300 rcf. The supernatant was filtered using a 0.20 μm filter and transferred into 6×1.5 ml tubes using 1 ml aliquots (rescue supernatant). The tubes were frozen at −80° C. till further processing or stored at 4° C. if passage of virions was performed at the same day of the rescue harvest.

Passage of Infectious Virions

HEK293-F or BHK21Cl.13 cells were seeded at 5×10$^6$ per 10 cm dish in 10 ml cDMEM one day before infection (d-1) or at 1×10$^7$ cells per 10 cm dish in the morning of transfection (d0) cultivated in the incubator at 37° C. Cells were approx. 80% confluent at day of infection with rescue supernatant.

1 ml of the rescue supernatant (stored at 4° C. until use or thawed about 30 min before infection) were added dropwise to each plate without disturbing the cell layer. The culture vessel was gently rocked back-and-forth and from side-to-side to evenly distribute the supernatant and cells were incubated in the incubator at 37° C. for 24 to 48 hours. As a negative control media may be added to one dish.

Harvest of Virus Seed Stocks

After 24 to 48 hours virus seed stocks were harvested if a clear cytopathic effect (CPE) is visible. Supernatant was taken of each dish and transferred into a 15 ml tube. Tubes were centrifuged for 4 minutes at 300 rcf. The supernatant was filtered using a 0.20 μm filter and 0.6 ml were transferred into 1.5 ml tubes using 1 ml aliquots (rescue supernatant). Tubes were frozen at −80° C. until plaque purification.

A generalized process summary is schematically provided in FIG. 2.

Example 1

HEK293-F cells are frequently used as suspension production cell line for VSV or recombinant VSV (rVSV, e.g., comprising genetically modified glycoprotein) production for clinical use as vaccine or gene therapy. For regulatory reasons it is advantageous to use the suspension production cell line also for helper-virus-free VSV or rVSV rescue from plasmids using transient transfection. However, we observed that VSV or rVSV was not effectively rescued using transient transfection in HEK293-F cells. HEK293T cells on the other hand, a related cell line known to be easily transfected and frequently used for virus production in a laboratory setting, was shown to be an effective cell line for VSV rescue.

In order to optimize VSV rescue in HEK293-F cells, viral protein expression was analysed in HEK293-F and HEK293T cells following transfection. HEK293-F and HEK293T cells were transiently transfected as adherent cells using 10 μg pVSV-LCMV GP, 2.4 μg pCAG VSV-N plasmid, 1.8 μg pCAG VSV-P plasmid, 0.6 μg pCAG VSV-L plasmid and 10 μg pCAGGS T7-RNAP IRES Puro as described above. Optionally 1 μg pCAG VSV-GP plasmid was added to the DNA-mixture for transfection or all NPL-Helper plasmids (pCAG VSV-N, pCAG VSV-P and pCAG VSV-L) were omitted as negative control, as indicated in FIG. 3.

Cell lysates were analysed by SDS page and Western Blot using polyclonal antibodies against P protein (FIG. 3, upper panel) and generic against VSV proteins (FIG. 3, lower panel) recognizing at least N, P and M protein. Since the P and M protein run as one band they cannot be distinguished using this serum. As positive control, VSV-GP virus purified by cation exchange chromatography (CEX) and concentrated by tangential flow filtration to 2.36×10$^{10}$ TCID50/ml (D-106-442) was used at 1 μl and 0.2 μl in separate lanes. No obvious differences in P protein and N protein expression in HEK293T and HEK293-F cells were observed (FIG. 3, lanes 1 and 4). T7 RNAP expression was not detected directly. Since P protein and N protein expression is not T7 RNAP dependent, the data suggest that no gross differences in transfection efficiency and expression of at least P protein and N protein can explain the differences observed for VSV rescue in HEK293-F and HEK293T cells.

Example 2

To analyse whether the SV40 large T antigen can support VSV rescue in HEK293-F cells, HEK293-F cells were transfected using the 5 plasmids for VSV rescue as described above in the absence or presence of the SV40 Large T antigen and with two different amounts of plasmid (1 μg and 5 μg). HEK293-F cells were cultured as adherent cells and transiently transfected using 10 μg pVSV-LCMV GP, 2.4 μg pCAG VSV-N plasmid, 1.8 μg pCAG VSV-P plasmid, 0.6 μg pCAG VSV-L plasmid and 10 μg pCAGGS T7-RNAP IRES Puro with (1 μg or 5 μg) or without the plasmid pCAG SV40 LargeT as described above. HEK293T cells were transfected the same way without co-transfection of the plasmid pCAG SV40 LargeT as control. Representative pictures at various time points are provided in FIG. 4A.

To confirm the production of infectious virus in HEK293-F and HEK293T cells, passages of harvest supernatants of the HEK293-F and HEK293T cells 48 h p.t. and 72 h p.t. were added to BHK21Cl.13 cells and analysed microscopically for cytopathic effects (CPE) 48 hours post-infection (p.i.). Surprisingly it has been found that transient transfection of HEK293-F cells with SV40 large T antigen allowed VSV or rVSV rescue. A clear cytopathic effect was visible in BHK21Cl.13 cells infected with harvest supernatants 48 h p.t. and 72 h p.t. from HEK293T cells and HEK293-F cells transiently transfected with SV40 Large T antigen, while no CPE was observed following infection with harvest supernatants 48 h p.t. and 72 h p.t. from HEK293-F cells in the absence of SV40 Large T antigen (FIG. 4B). 48 hours post infections, the BHK21Cl.13 cells infection with harvest supernatants 48 h p.t. and 72 h p.t. from HEK293-F cells in the absence of SV40 Large T antigen were indistinguishable from BHK21Cl.13 incubated with medium instead of harvest supernatant as a negative control. It can therefore be concluded that the presence of T antigen is required for infectious virus in HEK293-F cells.

Example 3

Figure 5B:
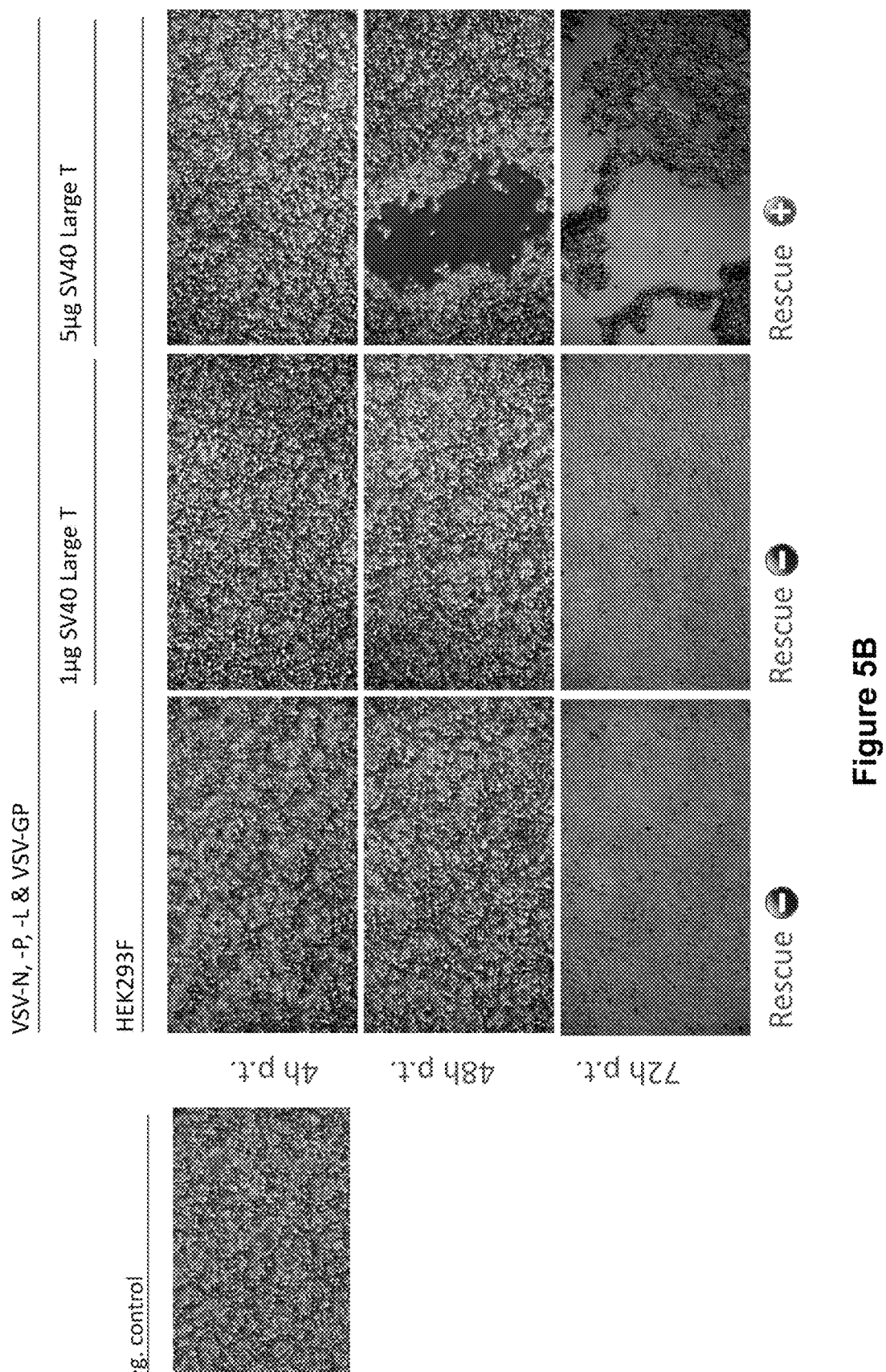

The previous experiment has been independently repeated using HEK293-F cells for the passage of infectious virions to confirm the successful rescue of VSV. HEK293-F cells were transfected with plasmids pVSV-LCMV GP (VSV-GP), pCAG VSV-N, pCAG VSV-P and pCAG VSV-L (VSV-N, -P, L) and pCAGGS T7-RNAP IRES Puro with (1 μg or 5 μg) or without (no SV40 Large T) co-transfection of plasmid pCAG SV40 LargeT. Representative pictures at various time points are provided in FIG. 5A. To confirm the production of infectious virus in HEK293-F cells, harvest supernatants of the HEK293-F cells 4 h p.t., 48 h p.t. and 72 h p.t. were added to 80% confluent adherent HEK293-F cells and analysed microscopically for cytopathic effects (CPE) 24 hours post-infection (p.i.). At his earlier time point using HEK293-F cells, a clear cytopathic effect (CPE) was visible in HEK293-F cells infected with harvest supernatants 48 h p.t. and 72 h p.t. from HEK293-F cells transiently transfected with 5 μg SV40 Large T antigen, while no CPE was observed following infection with harvest supernatants 48 h p.t. and 72 h p.t. from HEK293-F cells transiently transfected with 1 μg SV40 Large T antigen or in the absence of SV40 Large T antigen (FIG. 5B).

Example 4

The presence of the Large T antigen has been associated with an increased amplification of vectors containing the SV40 ori. The only plasmid used for VSV rescue comprising an SV40 ori is the plasmid encoding the T7-RNAP (pCAGGS T7-RNAP IRES Puro). Since the expression of the viral proteins N, P and L from the corresponding pCAG vectors is driven by the artificial CAG promoter and do not depend on the presence of the T polymerase, differences in viral protein levels do not explain the differences in viral recovery observed for HEK293T cells compared to HEK293-F cells (FIG. 3). However, we cannot exclude that T7 polymerase dependent primary transcription of the VSV-GP genomic RNA at the early step after plasmid transfection influences virus recovery in the different cell lines.

To analyse the effect of the SV40 ori in VSV rescue in HEK293-F cells in the presence of the T7-RNAP, we repeated VSV rescue in HEK293-F cells using a different vector not comprising an SV40 ori for T7-RNAP expression. The expression cassette encoding T7-RNAP derived from the plasmid pCAGGS T7-RNAP IRES Puro was therefore cloned into the pCAG plasmid used for VSV P protein, N protein and L protein expression. While efficacy was generally lower compared to the pCAGGS T7-RNAP IRES Puro, Large T antigen-dependent VSV rescue was still observed using the plasmid lacking an SV40 ori for T7-RNAP expression. Again VSV rescue was only observed in the presence of Large T antigen in HEK293-F cells.

SEQUENCE LISTING
SEQ ID NO: 1 (Vesicular stomatitis
Indiana virus, VSV-N):
MSVTVKRIIDNTVVVPKLPANEDPVEYPADYFRKS

KEIPLYINTTKSLSDLRGYVYQGLKSGNVSIIHVN

-continued
SYLYGALKDIRGKLDKDWSSFGINIGKAGDTIGIF

DLVSLKALDGVLPDGVSDASRTSADDKWLPLYLLG

LYRVGRTQMPEYRKKLMDGLTNQCKMINEQFEPLV

PEGRDIFDVWGNDSNYTKIVAAVDMFFHMFKKHEC

ASFRYGTIVSRFKDCAALATFGHLCKITGMSTEDV

TTWILNREVADEMVQMMLPGQEIDKADSYMPYLID

FGLSSKSPYSSVKNPAFHFWGQLTALLLRSTRARN

ARQPDDIEYTSLTTAGLLYAYAVGSSADLAQQFCV

GDNKYTPDDSTGGLTTNAPPQGRDVVEWLGWFEDQ

NRKPTPDMMQYAKRAVMSLQGLREKTIGKYAKSEF

DK

SEQ ID NO: 2 (Vesicular
stomatitis Indiana virus, VSV-P):
MDNLTKVREYLKSYSRLDQAVGEIDEIEAQRAEKS

NYELFQEDGVEEHTKPSYFQAADDSDTESEPEIED

NQGLYAPDPEAEQVEGFIQGPLDDYADEEVDVVFT

SDVVKQPELESDEHGKTLRLTSPEGLSGEQKSQWL

STIKAWQSAKYVVNLAECTFEASGEGVIMKERQIT

PDVYKVTPVMNTHPSQSEAVSDVWSLSKTSMTFQP

KKASLQPLTISLDELFSSRGEFISVGGDGRMSHKE

AILLGLRYKKLYNQARVKYSL

SEQ ID NO: 3 (Vesicular stomatitis
Indiana virus. VSV-L:
MEVHDFETDEFNDFNEDDYATREFLNPDERMTYLN

HADYNLNSPLISDDIDNLIRKFNSLPIPSMWDSKN

WDGVLEMLTSCQANPIPTSQMHKWMGSWLMSDNHD

ASQGYSFLHEVDKEAEITFDVVETFIRGWGNKPIE

YIKKERWTDSFKILAYLCQKFLDLHKLTLILNAVS

EVELLNLARTFKGKVRRSSHGTNICRIRVPSLGPT

FISEGWAYFKKLDILMDRNFLLMVKDVIIGRMQTV

LSMVCRIDNLFSEQDIFSLLNIYRIGDKIVERQGN

FSYDLIKMVEPICNLKLMKLARESRPLVPQFPHFE

NHIKTSVDEGAKIDRGIRFLHDQIMSVKTVDLTLV

IYGSFRHWGHPFIDYYTGLEKLHSQVTMKKDIDVS

YAKALASDLARIVLFQQFNDHKKWFVNGDLLPHDH

PFKSHVKENTWPTAAQVQDFGDKWHELPLIKCFEI

PDLLDPSIIYSDKSHSMNRSEVLKHVRMNPNTPIP

SKKVLQTMLDTKATNWKEFLKEIDEKGLDDDDLII

GLKGKERELKLAGRFFSLMSWKLREYFVITEYLIK

THFVPMFKGLTMADDLTAVIKKMLDSSSGQGLKSY

EAICIANHIDYEKWNNHQRKLSNGPVFRVMGQFLG

YPSLIERTHEFFEKSLIYYNGRPDLMRVHNNTLIN

STSQRVCWQGQEGGLEGLRQKGWSILNLLVIQREA

-continued

KIRNTAVKVLAQGDNQVICTQYKTKKSRNVVELQG

ALNQMVSNNEKIMTAIKIGTGKLGLLINDDETMQS

ADYLNYGKIPIFRGVIRGLETKRWSRVTCVTNDQI

PTCANIMSSVSTNALTVAHFAENPINAMIQYNYFG

TFARLLLMMHDPALRQSLYEVQDKIPGLHSSTFKY

AMLYLDPSIGGVSGMSLSRFLIRAFPDPVTESLSF

WRFIHVHARSEHLKEMSAVFGNPEIAKFRITHIDK

LVEDPTSLNIAMGMSPANLLKTEVKKCLIESRQTI

RNQVIKDATIYLYHEEDRLRSFLWSINPLFPRFLS

EFKSGTFLGVADGLISLFQNSRTIRNSFKKKYHRE

LDDLIVRSEVSSLTHLGKLHLRRGSCKMWTCSATH

ADTLRYKSWGRTVIGTTVPHPLEMLGPQHRKETPC

APCNTSGFNYVSVHCPDGIHDVFSSRGPLPAYLGS

KTSESTSILQPWERESKVPLIKRATRLRDAISWFV

EPDSKLAMTILSNIHSLTGEEWTKRQHGFKRTGSA

LHRFSTSRMSHGGFASQSTAALTRLMATTDTMRDL

GDQNFDFLFQATLLYAQITTTVARDGWITSCTDHY

HIACKSCLRPIEEITLDSSMDYTPPDVSHVLKTWR

NGEGSWGQEIKQIYPLEGNWKNLAPAEQSYQVGRC

IGFLYGDLAYRKSTHAEDSSLFPLSIQGRIRGRGF

LKGLLDGLMRASCCQVIHRRSLAHLKRPANAVYGG

LIYLIDKLSVSPPFLSLTRSGPIRDELETIPHKIP

TSYPTSNRDMGVIVRNYFKYQCRLIEKGKYRSHYS

QLWLFSDVLSIDFIGPFSISTTLLQILYKPFLSGK

DKNELRELANLSSLLRSGEGWEDIHVKFFTKDILL

CPEEIRHACKFGIAKDNNKDMSYPPWGRESRGTIT

TIPVYYTTTPYPKMLEMPPRIQNPLLSGIRLGQLP

TGAHYKIRSILHGMGIHYRDFLSCGDGSGGMTAAL

LRENVHSRGIFNSLLELSGSVMRGASPEPPSALET

LGGDKSRCVNGETCWEYPSDLCDPRTWDYFLRLKA

GLGLQIDLIVMDMEVRDSSTSLKIETNVRNYVHRI

LDEQGVLIYKTYGTYICESEKNAVTILGPMFKTVD

LVQTEFSSSQTSEVYMVCKGLKKLIDEPNPDWSSI

NESWKNLYAFQSSEQEFARAKKVSTYFTLTGIPSQ

FIPDPFVNIETMLQIFGVPTGVSHAAALKSSDRPA

DLLTISLFYMAIISYYNINHIRVGPIPPNPPSDGI

AQNVGIAITGISFWLSLMEKDIPLYQQCLAVIQQS

FPIRWEAVSVKGGYKQKWSTRGDGLPKDTRISDSL

-continued

APIGNWIRSLELVRNQVRLNPFNEILFNQLCRTVD

NHLKWSNLRRNTGMIEWINRRISKEDRSILMLKSD

LHEENSWRD

SEQ ID NO: 4 (T7 RNA polymerase):
MNTINIAKNDFSDIELAAIPFNTLADHYGERLARE

QLALEHESYEMGEARFRKMFERQLKAGEVADNAAA

KPLITTLLPKMIARINDWFEEVKAKRGKRPTAFQF

LQEIKPEAVAYITIKTTLACLTSADNTTVQAVASA

IGRAIEDEARFGRIRDLEAKHFKKNVEEQLNKRVG

HVYKKAFMQVVEADMLSKGLLGGEAWSSWHKEDSI

HVGVRCIEMLIESTGMVSLHRQNAGVVGQDSETIE

LAPEYAEAIATRAGALAGISPMFQPCVVPPKPWTG

ITGGGYWANGRRPLALVRTHSKKALMRYEDVYMPE

VYKAINIAQNTAWKINKKVLAVANVITKWKHCPVE

DIPAIEREELPMKPEDIDMNPEALTAWKRAAAVY

RKDKARKSRRISLEFMLEQANKFANHKAIWFPYNM

DWRGRVYAVSMFNPQGNDMTKGLLTLAKGKPIGKE

GYYWLKIHGANCAGVDKVPFPERIKFIEENHENIM

ACAKSPLENTWWAEQDSPFCFLAFCFEYAGVQHHG

LSYNCSLPLAFDGSCSGIQHFSAMLRDEVGGRAVN

LLPSETVQDIYGIVAKKVNEILQADAINGTDNEWT

VTDENTGEISEKVKLGTKALAGQWLAYGVTRSVTK

RSVMTLAYGSKEFGFRQQVLEDTIQPAIDSGKGLM

FTQPNQAAGYMAKLIWESVSVTVVAAVEAMNWLKS

AAKLLAAEVKDKKTGEILRKRCAVHWVTPDGFPVW

QEYKKPIQTRLNLMFLGQFRLQPTINTNKDSEIDA

HKQESGIAPNFVHSQDGSHLRKTVVWAHEKYGIES

FALIHDSFGTIPADAANLFKAVRETMVDTYESCDV

LADFYDQFADQLHESQLDKMPALPAKGNLNLRDIL

ESDFAFA

SEQ ID NO: 5 (Simian virus 40,
SV40 Large T antigen):
IPTYGTDEWEQWWNAFNEENLFCSEEMPSSDDEAT

ADSQHSTPPKKKRKVEDPKDFPSELLSFLSHAVFS

NRTLACFAIYTTKEKAALLYKKIMEKYSVTFISRH

NSYNHNILFFLTPHRHRVSAINNYAQKLCTFSFLI

CKGVNKEYLMYSALTRDPFSVIEESLPGGLKEHDF

NPEEAEETKQVSWKLVTEYAMETKCDDVLLLLGMY

LEFQYSFEMCLKCIKKEQPSHYKYHEKHYANAAIF

ADSKNQKTICQQAVDTVLAKKRVDSLQLTREQMLT

NRFNDLLDRMDIMFGSTGSADIEEWMAGVAWLHCL

LPKMDSVVYDFLKCMVYNIPKKRYWLFKGPIDSGK

-continued

TTLAAALLELCGGKALNVNLPLDRLNFELGVAIDQ

FLWFEDVKGTGGESRDLPSGQGINNLDNLRDYLDG

SVKVNLEKKHLNKRTQIFPPGIVTMNEYSVPKTLQ

ARFVKQIDFRPKDYLKHCLERSEFLLEKRIIQSGI

ALLLMLIWYRPVAEFAQSIQSRIVEWKERLDKEFS

LSVYQKMKFNVAMGIGVLDWLRNSDDDDEDSQENA

DKNEDGGEKNMEDSGHETGIDSQSQGSFQAPQSSQ

SVHDHNQPYHICRGFTCFKKPPTPPPEPET

SEQ ID NO: 6
(Vesicular stomatitis Indiana virus
strain T1026R1 complete sequence):
tcaggagaaacttttaacagtaatcaaaatgtctgt tacagtcaagagaatcattgacaacacagtcatag ttccaaaacttcctgcaaatgaggatccagtggaa tacccggcagattacttcagaaaatcaaaggagat tcctctttacatcaatactacaaaaagtttgtcag atctaagaggatatgtctaccaaggcctcaaatcc ggaaatgtatcaatcatacatgtcaacagctactt gtatggagcattgaaggacatccggggtaagttgg ataaagattggtcaagtttcggaataaacatcggg aaggcagggggatacaatcggaatatttgaccttgt atccttgaaagccctggacggtgtacttccagatg gagtatcggatgcttccagaaccagcgcagatgac aaatggttgcctttgtatctacttggcttatacag agtgggcagaacacaaatgcctgaatacagaaaaa ggctcatggatgggctgacaaatcaatgcaaaatg atcaatgaacagtttgaacctcttgtgccagaagg tcgtgacattttgatgtgtgtgggaaatgacagta attacacaaaaattgtcgctgcagtggacatgttc ttccacatgttcaaaaaacatgaatgtgcctcgtt cagatacggaactattgtttccagattcaaagatt gtgctgcattggcaacatttggacacctctgcaaa ataaccggaatgtctacagaagatgtaacgacctg gatcttgaaccgagaagttgcagatgagatggtcc aaatgatgcttccaggccaagaaattgacaaggcc gattcatacatgccttatttgatcgactttggatt gtcttctaagtctccatattcttccgtcaaaaacc ctgccttccacttctgggggcaattgacagctctt ctgctcagatccaccagagcaaggaatgcccgaca gcctgatgacattgagtatacatctcttactacag caggtttgttgtacgcttatgcagtaggatcctct gctgacttggcacaacagttttgtgttggagatag -continued caaatacactccagatgatagtaccggaggattga cgactaatgcaccgccacaaggcagagatgtggtc gaatggctcggatggtttgaagatcaaaacagaaa accgactcctgatatgatgcagtatgcgaaacgag cagtcatgtcactgcaaggcctaagagagaagaca attggcaagtatgctaagtcagaatttgacaaatg accctataattctcagatcacctattatatattat gctacatatgaaaaaaactaacagatatcatggat aatctcacaaaagttcgtgagtatctcaagtccta ttctcgtctagatcaggcggtaggagagatagatg agatcgaagcacaacgagctgaaaagtccaattat gagttgttccaagaggacggagtggaagagcatac taggccctcttattttcaggcagcagatgattctg acacagaatctgaaccagaaattgaagacaatcaa ggcttgtatgtaccagatccggaagctgagcaagt tgaaggctttatacaggggcctttagatgactatg cggatgaggacgtggatgttgtattcacttcggac tggaaacagcctgagcttgaatccgacgagcatgg aaagaccttacggttgacattgccagagggtttaa gtggagagcagaaatcccagtggcttttgacgatt aaagcagtcgttcaaagtgccaaacactggaatct ggcagagtgcacatttgaagcatcgggagaagggg tcatcataaaaaaagcgccagataactccggatgta tataaggtcactccagtgatgaacacacatccgtc ccaatcggaagccgtatcagatgtttggtctctct caaagacatccatgactttccaacccaagaaagca agtcttcagcctctcaccatatccttggatgaatt gttctcatctagaggagaattcatctctgtcggag gtaacggacgaatgtctcataaagaggccatcctg ctcggtctgaggtacaaaaagttgtacaatcaggc gagagtcaaatattctctgtagactatgaaaaaaa gtaacagatatcacaatctaagtgttatcccaatc cattcatcatgagttccttaaagaagattctcggt ctgaaggggaaaggtaagaaatctaagaaattagg gatcgcaccacccccttatgaagaggacactaaca tggagtatgctccgagcgctccaattgacaaatcc tattttggagttgacgagagggacactcatgatcc gcatcaattaagatatgagaaattcttcttttacag tgaaaatgacggttagatctaatcgtccgttcaga acatactcagatgtggcagccgctgtatcccattg ggatcacatgtacatcggaatggcagggaaacgtc -continued

```
ccttctacaagatcttggctttttttgggttcttct aatctaaaggccactccagcggtattggcagatca aggtcaaccagagtatcacgctcactgtgaaggca gggcttatttgccacacagaatggggaagacccct cccatgctcaatgtaccagagcacttcagaagacc attcaatataggtctttacaagggaacggttgagc tcacaatgaccatctacgatgatgagtcactggaa gcagctcctatgatctgggatcatttcaattcttc caaattttctgatttcagagagaaggccttaatgt ttggcctgattgtcgagaaaaaggcatctggagct tgggtcctggattctgtcagccacttcaaatgagc tagtctagcttccagcttctgaacaatccccggtt tactcagtctctcctaattccagcctttcgaacaa ctaatatcctgtcttttctatccctatgaaaaaaa ctaacagagatcgatctgtttccttgacaccatga agtgccttttgtacttagcttttttattcatcggg gtgaattgcaagttcaccatagtttttccatacaa ccaaaaaggaaactggaaaaatgttccttccaatt accattattgcccgtcaagctcagatttaaattgg cataatgacttaataggcacagccttacaagtcaa aatgcccaagagtcacaaggctattcaagcagacg gttggatgtgtcatgcttccaaatgggtcactact tgtgatttccgctggtacggaccgaagtatataac acattccatccgatccttcactccatctgtagaac aatgcaaggaaagcattgaacaaacgaaacaagga acttggctgaatccaggcttcctcctcaaagttg tggatatgcaactgtgacggatgctgaagcagcga ttgtccaggtgactcctcaccatgtgcttgttgat gaatacacaggagaatgggttgattcacagttcat caacggaaaatgcagcaatgacatatgccccactg tccataactccacaacctggcattccgactataag gtcaaagggctatgtgattctaacctcatttccat ggacatcaccttcttctcagaggacggagagctat catccctaggaaaggagggcacagggttcagaagt aactactttgcttatgaaactggagacaaggcctg caaaatgcagtactgcaagcattggggagtcagac tcccatcaggtgtctggttcgagatggctgataag gatctctttgctgcagccagattccctgaatgccc agaagggtcaagtatctctgctccatctcagacct cagtggatgtaagtctcattcaggacgttgagagg
```

-continued

```
atcttggattattccctctgccaagaaacctggag caaaatcagagcgggtcttcccatctctccagtgg atctcagctatcttgctcctaaaaacccaggaacc ggtcctgtctttaccataatcaatggtaccctaaa atactttgagaccagatacatcagagtcgatattg ctgctccaatcctctcaagaatggtcggaatgatc agtggaactaccacagaaagggaactgtgggatga ctgggctccatatgaagacgtggaaattggaccca atggagttctgaggaccagttcaggatataagttt cctttatatatgattggacatggtatgttggactc cgatcttcatcttagctcaaaggctcaggtgtttg aacatcctcacattcaagacgctgctgcgcagctt cctgatgatgagactttattttttggtgatactgg gctatccaaaaatccaatcgagtttgtagaaggtt ggttcagtagttggaagagctctattgcctctttt ttctttatcatagggttaatcattggactattctt ggttctccgagttggtatttatctttgcattaaat taaagcacaccaagaaaagacagatttatacagac atagagatgaaccgacttgggaagtaactcaaatc ctgcacaacagattcttcatgtttgaaccaaatca acttgtgatatcatgctcaaagaggccttaattat attttaatttttaattttttatgaaaaaaactaaca gcaatcatggaagtccacgattttgagaccgacga gttcaatgatttcaatgaagatgactatgccacaa gagaattcctgaatcccgatgagcgcatgacgtac ttgaatcatgctgattacaatttgaattctcctct aattagtgatgatattgacaatttgatcaggaaat tcaattctcttccgattccctcgatgtgggatagt aagaactgggatggagttcttgagatgttaacatc atgtcaagccaatcccatctcaacatctcagatgc ataaatggatgggaagttggttaatgtctgataat catgatgccagtcaagggtatagttttttacatga agtggacaaagaggcagaaataacatttgacgtgg tggagaccttcatccgcggctggggcaacaaacca attgaatacatcaaaaaggaaagatggactgactc attcaaaattctcgcttatttgtgtcaaaagtttt tggacttacacaagttgacattaatcttaaatgct gtctctgaggtggaattgctcaacttggcgaggac tttcaaaggcaaagtcagaagaagttctcatggaa cgaacatatgcaggcttaggggttcccagcttgggt cctactttttatttcagaaggatgggcttacttcaa
```

-continued gaaacttgatattctaatggaccgaaactttctgt taatggtcaaagatgtgattatagggaggatgcaa acggtgctatccatggtatgtagaatagacaacct gttctcagagcaagacatcttctccctcctaaata tctacagaattggagataaaattgtggagaggcag ggaaattttctttatgacttgattaaaatggtgga accgatatgcaacttgaagctgatgaaattagcaa gagaatcaaggcctttagtcccacaattccctcat tttgaaaatcatatcaagacttctgttgatgaagg ggcaaaaattgaccgaggtataagattcctccatg atcagataatgagtgtgaaaacagtggatctcaca ctggtgatttatggatcgttcagacattgggggtca tccttttatagattattacgctggactagaaaaat tacattcccaagtaaccatgaagaaagatattgat gtgtcatatgcaaaagcacttgcaagtgatttagc tcggattgttctatttcaacagttcaatgatcata aaaagtggttcgtgaatggagacttgctccctcat gatcatccctttaaaagtcatgttaaagaaaatac atggcccacagctgctcaagttcaagattttggag ataaatggcatgaacttccgctgattaaatgtttt gaaatacccgacttactagacccatcgataatata ctctgacaaaagtcattcaatgaataggtcagagg tgttgaaacatgtccgaatgaatccgaacactcct atccctagtaaaaaggtgttgcagactatgttgga cacaaaggctaccaattggaaagaatttcttaaag agattgatgagaagggcttagatgatgatgatcta attattggtcttaaaggaaaggagagggaactgaa gttggcaggtagattttttctccctaatgtcttgga aattgcgagaatactttgtaattaccgaatatttg ataaagactcatttcgtccctatgtttaaaggcct gacaatggcggacgatctaaccgcagtcattaaaa agatgttagattcctcatccggccaaggattgaag tcatatgaggcaatttgcatagccaatcacattga ttacgaaaaatggaataaccaccaaaggaagttat caaacggcccagtgttccgagttatgggccagttc ttaggttatccatccttaatcgagagaactcatga atttttttgagaaaagtcttatatactacaatggaa gaccagacttgatgcgtgttcacaacaacacactg atcaattcaacctcccaacgagtttgttggcaagg acaagagggtggactggaaggtctacggcaaaaag -continued gatggagtatcctcaatctactggttattcaaaga gaggctaaaatcagaaacactgctgtcaaagtctt ggcacaaggtgataatcaagttatttgcacacagt ataaaacgaagaaatcgagaaacgttgtagaatta cagggtgctctcaatcaaatggtttctaataatga gaaaattatgactgcaatcaaaatagggacaggga agttaggacttttgataaatgacgatgagactatg caatctgcagattacttgaattatggaaaaatacc gattttccgtggagtgattagagggttagagacca agagatggtcacgagtgacttgtgtcaccaatgac caaatacccacttgtgctaatataatgagctcagt ttccacaaatgctctcaccgtagctcattttgctg agaacccaatcaatgccatgatacagtacaattat tttgggacatttgctagactcttgttgatgatgca tgatcctgctcttcgtcaatcattgtatgaagttc aagataagataccgggattgcacagttctactttc aaatacgccatgttgtatttggacccttccattgg aggagtgtcgggcatgtctttgtccaggttttttga ttagagccttcccagatcccgtaacagaaagtctc tcattctggagattcatccatgtacatgctcgaag tgagcatctgaaggagatgagtgcagtatttggaa accccgagatagccaagtttcgaataactcacata gacaagctagtagaagatccaacctctctgaacat cgctatgggaatgagtccagcgaacttgttaaaga ctgaggttaaaaaatgcttaatcgaatcaagacaa accatcaggaaccaggtgattaaggatgcaaccat atatttgtatcatgaagaggatcggctcagaagtt tcttatggtcaataaatcctctgttccctagatttt ttaagtgaattcaaatcaggcacttttttgggagt cgcagacgggctcatcagtctatttcaaaattctc gtactattcggaactcctttaagaaaaagtatcat agggaattggatgatttgattgtgaggagtgaggt atcctcttttgacacatttagggaaacttcatttga gaagggatcatgtaaaatgtggacatgttcagct actcatgctgacacattaagatacaaatcctgggg ccgtacagttattgggacaactgtaccccatccat tagaaatgttgggtccacaacatcggaaagagact ccttgtgcaccatgtaacacatcaggttcaatta tgtttctgtgcattgtccagacgggatccatgacg tctttagttcacggggaccattgcctgcttatcta gggtctaaaacatctgaatctacatctattttgca

31 gccttgggaaagggaaagcaaagtcccactgatta aaagagctacacgtcttagagatgctatctcttgg tttgttgaacccgactctaaactagcaatgactat actttctaacatccactctttaacaggcgaagaat ggaccaaaaggcagcatgggttcaaaagaacaggg tctgcccttcataggttttcgacatctcggatgag ccatggtgggttcgcatctcagagcactgcagcat tgaccaggttgatggcaactacagacaccatgagg gatctgggagatcagaatttcgactttttattcca ggcaacgttgctctatgctcagattaccaccactg ttgcaagagacggatggatcaccagttgtacagat cattatcatattgcctgtaagtcctgtttgagacc catagaagagatcaccctggactcaagtatggact acacgcccccagatgtatcccatgtgctgaagaca tggaggaatgggaaggttcgtggggacaagagat aaaacagatctatcctttagaagggaattggaaga atttagcacctgctgagcaatcctatcaagtcggc agatgtataggttttctatatggagacttggcgta tagaaaatctactcatgccgaggacagttctctat ttcctctatctatacaaggtcgtattagaggtcga ggtttcttaaaagggttgctagacggattaatgag agcaagttgctgccaagtaatacaccggagaagtc tggctcatttgaagaggccggccaacgcagtgtac ggaggtttgatttacttgattgataaattgagtgt atcacctccattcctttctcttactagatcaggac ctattagagacgaattagaaacgattccccacaag atcccaacctcctatccgacaagcaaccgtgatat gggggtgattgtcagaaattacttcaaataccaat gccgtctaattgaaaaggggaaaatacagatcacat tattcacaattatggttattctcagatgtcttatc catagacttcattggaccattctctatttccacca ccctcttgcaaatcctatacaagccattttttatct gggaaagataagaatgagttgagagagctggcaaa tctttcttcattgctaagatcaggagaggggtggg aagacatacatgtgaaattcttcaccaaggacata ttattgtgtccagaggaaatcagacatgcttgcaa gttcgggattgctaaggataataataaagacatga gctatcccccttggggaagggaatccagagggaca attacaacaatccctgtttattatacgaccacccc ttacccaaagatgctagagatgcctccaagaatcc

32 aaaatcccctgctgtccggaatcaggttgggccag ttaccaactggcgctcattataaaaattcggagtat attacatggaatgggaatccattacagggacttct tgagttgtgggagacggctccggagggatgactgct gcattactacgagaaaatgtgcatagcagaggaat attcaatagtctgttagaattatcagggtcagtca tgcgaggcgcctctcctgagcccccccagtgccta gaaactttaggaggagataaatcgagatgtgtaaa tggtgaaacatgttgggaatatccatctgacttat gtgacccaaggacttgggactatttcctccgactc aaagcaggcttggggcttcaaattgatttaattgt aatggatatggaagttcgggattcttctactagcc tgaaaattgagacgaatgttagaaattatgtgcac cggattttggatgagcaaggagttttaatctacaa gacttatggaacatatatttgtgagagcgaaaaga atgcagtaacaatccttggtcccatgttcaagacg gtcgacttagttcaaacagaatttagtagttctca aacgtctgaagtatatatggtatgtaaaggtttga agaaattaatcgatgaacccaatcccgattggtct tccatcaatgaatcctggaaaaacctgtacgcatt ccagtcatcagaacaggaatttgccagagcaaaga aggttagtacatactttaccttgacaggtattccc tcccaattcattcctgatcctttgtaaacattga gactatgctacaaatattcggagtacccacgggtg tgtctcatgcggctgccttaaaatcatctgataga cctgcagatttattgaccattagcctttttttatat ggcgattatatcgtattataacatcaatcatatca gagtaggaccgatacctccgaacccccccatcagat ggaattgcacaaaatgtggggatcgctataactgg tataagcttttggctgagtttgatggagaaagaca ttccactatatcaacagtgtttagcagttatccag caatcattcccgattaggtgggaggctgtttcagt aaaaggaggatacaagcagaagtggagtactagag gtgatgggctcccaaaggatacccgaatttcagac tccttggccccaatcgggaactggatcagatctct ggaattggtccgaaaccaagttcgtctaaatccat tcaatgagatcttgttcaatcagctatgtcgtaca gtggataatcatttgaaatggtcaaatttgcgaaa aaacacaggaatgattgaatggatcaatagacgaa tttcaaaagaagaccggtctatactgatgttgaag agtgacctacatgaggaaaactcttggagagatta -continued

```
aaaaatcatgaggagactccaaactttaagtatga aaaaaactttgatccttaagaccctcttgtggttt ttattttttatctggttttg SEQ ID NO: 7
(Lymphocytic choriomeninqitis virus,
LCMV GP):
MGQIVTMFEALPHIIDEVINIVIIVLIIITSIKAV

YNFATCGILALVSFLFLAGRSCGMYGLNGPDIYKG

VYQFKSVEFDMSHLNLTMPNACSANNSHHYISMGS

SGLELTFTNDSILNHNFCNLTSAFNKKTFDHTLMS

IVSSLHLSIRGNSNHKAVSCDFNNGITIQYNLSFS
```

-continued

```
DPQSAISQCRTFRGRVLDMFRTAFGGKYMRSGWGW

AGSDGKTTWCSQTSYQYLIIQNRTWENHCRYAGPF

GMSRILFAQEKTKFLTRRLAGTFTWTLSDSSGVEN

PGGYCLTKWMILAAELKCFGNTAVAKCNVNHDEEF

CDMLRLIDYNKAALSKFKQDVESALHVFKTTVNSL

ISDQLLMRNHLRDLMGVPYCNYSKFWYLEHAKTGE

TSVPKCWLVTNGSYLNETHFSDQIEQEADNMITEM

LRKDYIKRQGSTPLALMDLLMFSTSAYLISIFLHL

VKIPTHRHIKGGSCPKPHRLTNKGICSCGAFKVPG

VKTIWKRR
```

The invention claimed is:

1. A method for rescue of Vesicular Stomatitis Virus (VSV) from DNA in a HEK293 cell line or a HEK293 cell line adapted to suspension growth comprising (a) providing cells from a HEK293 cell line or a HEK293 cell line adapted to suspension growth in cell culture, (b) transiently transfecting the cells with at least one plasmid, wherein the at least one plasmid comprises (i) an expression cassette comprising a VSV genomic cDNA;

(ii) at least one expression cassette encoding VSV nucleoprotein (N) protein, VSV phosphoprotein (P) protein and VSV large (L) protein; and (iii) an expression cassette encoding SV40 Large T antigen;

(c) culturing the transfected cells; and (d) harvesting the cell culture supernatant comprising the rescued VSV 24 hours to 96 hours post transfection.

2. The method according to claim 1, wherein the harvested cell culture supernatant comprises infectious VSV.

3. The method according to claim 1, wherein (i) the cells are provided, transfected and cultured as adherent cells; and/or (ii) transfecting the cells in step (b) comprises the use of a chemical-based transfection agent, preferably wherein the chemical-based transfection agent is selected from Lipofection, PEI or calcium phosphate.

4. The method according to claim 1, wherein the cells in step (b) are further transfected or transduced with a plasmid or a helper virus comprising an expression cassette encoding bacteriophage T7 RNA polymerase under the control of an RNA polymerase II-dependent promoter; and wherein the expression cassette comprising the VSV genomic cDNA comprises the VSV genomic cDNA under the control of a T7 promoter and a T7 terminator sequence; and optionally wherein the at least one expression cassette encoding VSV N protein, VSV P protein and VSV L protein comprises the VSV N, P and/or L protein under the control of a promoter and a terminator sequence.

5. The method according to claim 4, wherein the method is a helper-virus free method and wherein the cells in step (b) are transfected with the plasmid comprising an expression cassette encoding bacteriophage T7 RNA polymerase under the control of an RNA polymerase II-dependent promoter.

6. The method according to claim 4, wherein (a) nucleotide sequence encoding the bacteriophage T7 RNA polymerase is codon-optimized; and/or (b) the bacteriophage T7 RNA polymerase has the amino acid sequence of SEQ ID NO: 4 or has at least 95% sequence identity with the amino acid sequence or SEQ ID NO: 4.

7. The method according to claim 1, wherein the at least one expression cassette encoding the VSV P protein, VSV N protein and VSV L protein is transfected as one or more helper plasmids.

8. The method according to claim 7, wherein the one or more helper plasmid comprises (i) a first helper plasmid comprising an expression cassette comprising a sequence encoding the VSV N protein under the control of a promoter and a terminator sequence;

(ii) a second helper plasmid comprising an expression cassette comprising a sequence encoding the VSV P protein under the control of a promoter and a terminator sequence; and (iii) a third helper plasmid comprising an expression cassette comprising a sequence encoding the VSV L protein under the control of a promoter and a terminator sequence; and optionally (iv) at least one further helper plasmid comprising an expression cassette comprising a sequence encoding the VSV glycoprotein (G) and/or an expression cassette comprising a sequence encoding the VSV matrix (M) protein.

9. The method according to claim 1, wherein the expression cassette encoding the SV40 Large T antigen (a) is transfected as a plasmid comprising said expression cassette encoding SV40 Large T antigen;

(b) comprises the nucleic acid sequence encoding the SV40 Large T antigen under the control of a promoter and further comprises a terminator sequence;

(c) comprises the nucleic acid sequence encoding the SV40 Large T antigen under the control of a promoter and further comprises a terminator sequence under the control of a strong RNA polymerase II-dependent promoter; and/or (d) comprises a nucleic acid sequence encoding the SV40 large T antigen having an amino acid sequence of SEQ ID NO: 5 or having at least 95% sequence identity with the amino acid sequence of SEQ ID NO: 5.

10. The method according to claim 1, wherein the HEK293 cell line or HEK293 cell line adapted to suspension growth is selected from the group consisting of HEK293, HEK293-F and HEK-293-H.

11. The method according to claim 10, wherein the HEK293 cell line or HEK293 cell line adapted to suspension growth is HEK293-F.

12. The method according to claim 1, wherein the VSV genomic cDNA is a viral full-length genomic cDNA, a modified viral genomic cDNA, or a modified, full-length genomic cDNA.

13. The method according to claim 1, wherein the VSV genomic cDNA is a modified viral genomic cDNA encoding a modified G protein.

14. The method according to claim 13, wherein the gene coding for the glycoprotein G in the VSV genomic cDNA is replaced by a gene coding for the glycoprotein GP of Lymphocyte choriomeningitis virus (LCMV).

15. The method according to claim 1, further comprising (e) transducing cells from a HEK293 cell line or a HEK293 cell line adapted to suspension growth in suspension with VSV obtained in step (d); and optionally (f) producing VSV in the cells of step (e) in suspension culture at >50 L.

16. The method according to claim 1, wherein the cells in part (a) are from a HEK293 cell line adapted to suspension growth.

17. The method according to claim 16, wherein the cells from the HEK293 cell line adapted to suspension growth are selected from the group consisting of HEK293-F and HEK-293-H.

18. The method according to claim 14, wherein the gene coding for the glycoprotein G in the VSV genomic cDNA is replaced by a gene coding for the glycoprotein GP of Lymphocyte choriomeningitis virus (LCMV) that comprises an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7.

* * * * *

SEQUENCE LISTING

```
Sequence total quantity: 7
SEQ ID NO: 1              moltype = AA  length = 422
FEATURE                   Location/Qualifiers
REGION                    1..422
                          note = VSV-N
source                    1..422
                          mol_type = protein
                          organism = Vesicular stomatitis Indiana virus
SEQUENCE: 1
MSVTVKRIID NTVVVPKLPA NEDPVEYPAD YFRKSKEIPL YINTTKSLSD LRGYVYQGLK  60
SGNVSIIHVN SYLYGALKDI RGKLDKDWSS FGINIGKAGD TIGIFDLVSL KALDGVLPDG  120
VSDASRTSAD DKWLPLYLLG LYRVGRTQMP EYRKKLMDGL TNQCKMINEQ FEPLVPEGRD  180
IFDVWGNDSN YTKIVAAVDM FFHMFKKHEC ASFRYGTIVS RFKDCAALAT FGHLCKITGM  240
STEDVTTWIL NREVADEMVQ MMLPGQEIDK ADSYMPYLID FGLSSKSPYS SVKNPAFHFW  300
GQLTALLLRS TRARNARQPD DIEYTSLTTA GLLYAYAVGS SADLAQQFCV GDNKYTPDDS  360
TGGLTTNAPP QGRDVVEWLG WFEDQNRKPT PDMMQYAKRA VMSLQGLREK TIGKYAKSEF  420
DK                                                                422

SEQ ID NO: 2              moltype = AA  length = 265
FEATURE                   Location/Qualifiers
REGION                    1..265
                          note = VSV-P
source                    1..265
                          mol_type = protein
                          organism = Vesicular stomatitis Indiana virus
SEQUENCE: 2
MDNLTKVREY LKSYSRLDQA VGEIDEIEAQ RAEKSNYELF QEDGVEEHTK PSYFQAADDS  60
DTESEPEIED NQGLYAPDPE AEQVEGFIQG PLDDYADEEV DVVFTSDWKQ PELESDEHGK  120
TLRLTSPEGL SGEQKSQWLS TIKAVVQSAK YWNLAECTFE ASGEGVIMKE RQITPDVYKV  180
TPVMNTHPSQ SEAVSDVWSL SKTSMTFQPK KASLQPLTIS LDELFSSRGE FISVGGDGRM  240
SHKEAILLGL RYKKLYNQAR VKYSL                                        265

SEQ ID NO: 3              moltype = AA  length = 2109
FEATURE                   Location/Qualifiers
REGION                    1..2109
                          note = VSV-L
source                    1..2109
                          mol_type = protein
                          organism = Vesicular stomatitis Indiana virus
SEQUENCE: 3
MEVHDFETDE FNDFNEDDYA TREFLNPDER MTYLNHADYN LNSPLISDDI DNLIRKFNSL  60
PIPSMWDSKN WDGVLEMLTS CQANPIPTSQ MHKWMGSWLM SDNHDASQGY SFLHEVDKEA  120
EITFDVVETF IRGWGNKPIE YIKKERWTDS FKILAYLCQK FLDLHKLTLI LNAVSEVELL  180
NLARTFKGKV RRSSHGTNIC RIRVPSLGPT FISEGWAYFK KLDILMDRNF LLMVKDVIIG  240
RMQTVLSMVC RIDNLFSEQD IFSLLNIYRI GDKIVERQGN FSYDLIKMVE PICNLKLMKL  300
ARESRPLVPQ FPHFENHIKT SVDEGAKIDR GIRFLHDQIM SVKTVDLTLV IYGSFRHWGH  360
PFIDYYTGLE KLHSQVTMKK DIDVSYAKAL ASDLARIVLF QQFNDHKKWF VNGDLLPHDH  420
PFKSHVKENT WPTAAQVQDF GDKWHELPLI KCFEIPDLLD PSIIYSDKSH SMNRSEVLKH  480
VRMNPNTPIP SKKVLQTMLD TKATNWKEFL KEIDEKGLDD DDLIIGLKGK ERELKLAGRF  540
FSLMSWKLRE YFVITEYLIK THFVPMFKGL TMADDLTAVI KKMLDSSSGQ GLKSYEAICI  600
ANHIDYEKWN NHQRKLSNGP VFRVMGQFLG YPSLIERTHE FFEKSLIYYN GRPDLMRVHN  660
NTLINSTSQR VCWQGQEGGL EGLRQKGWSI LNLLVIQREA KIRNTAVKVL AQGDNQVICT  720
QYKTKKSRNV VELQGALNQM VSNNEKIMTA IKIGTGKLGL LINDDETMQS ADYLNYGKIP  780
IFRGVIRGLE TKRWSRVTCV TNDQIPTCAN IMSSVSTNAL TVAHFAENPI NAMIQYNYFG  840
```

```
TFARLLLMMH DPALRQSLYE VQDKIPGLHS STFKYAMLYL DPSIGGVSGM SLSRFLIRAF  900
PDPVTESLSF WRFIHVHARS EHLKEMSAVF GNPEIAKFRI THIDKLVEDP TSLNIAMGMS  960
PANLLKTEVK KCLIESRQTI RNQVIKDATI YLYHEEDRLR SFLWSINPLF PRFLSEFKSG 1020
TFLGVADGLI SLFQNSRTIR NSFKKKYHRE LDDLIVRSEV SSLTHLGKLH LRRGSCKMWT 1080
CSATHADTLR YKSWGRTVIG TTVPHPLEML GPQHRKETPC APCNTSGFNY VSVHCPDGIH 1140
DVFSSRGPLP AYLGSKTSES TSILQPWERE SKVPLIKRAT RLRDAISWFV EPDSKLAMTI 1200
LSNIHSLTGE EWTKRQHGFK RTGSALHRFS TSRMSHGGFA SQSTAALTRL MATTDTMRDL 1260
GDQNFDFLFQ ATLLYAQITT TVARDGWITS CTDHYHIACK SCLRPIEEIT LDSSMDYTPP 1320
DVSHVLKTWR NGEGSWGQEI KQIYPLEGNW KNLAPAEQSY QVGRCIGFLY GDLAYRKSTH 1380
AEDSSLFPLS IQGRIRGRGF LKGLLDGLMR ASCCQVIHRR SLAHLKRPAN AVYGGLIYLI 1440
DKLSVSPPFL SLTRSGPIRD ELETIPHKIP TSYPTSNRDM GVIVRNYFKY QCRLIEKGKY 1500
RSHYSQLWLF SDVLSIDFIG PFSISTTLLQ ILYKPFLSGK DKNELRELAN LSSLLRSGEG 1560
WEDIHVKFFT KDILLCPEEI RHACKFGIAK DNNKDMSYPP WGRESRGTIT TIPVYYTTTP 1620
YPKMLEMPPR IQNPLLSGIR LGQLPTGAHY KIRSILHGMG IHYRDFLSCG DGSGGMTAAL 1680
LRENVHSRGI FNSLLELSGS VMRGASPEPP SALETLGGDK SRCVNGETCW EYPSDLCDPR 1740
TWDYFLRLKA GLGLQIDLIV MDMEVRDSST SLKIETNVRN YVHRILDEQG VLIYKTYGTY 1800
ICESEKNAVT ILGPMFKTVD LVQTEFSSSQ TSEVYMVCKG LKKLIDEPNP DWSSINESWK 1860
NLYAFQSSEQ EFARAKKVST YFTLTGIPSQ FIPDPFVNIE TMLQIFGVPT GVSHAAALKS 1920
SDRPADLLTI SLFYMAIISY YNINHIRVGP IPPNPPSDGI AQNVGIAITG ISFWLSLMEK 1980
DIPLYQQCLA VIQQSFPIRW EAVSVKGGYK QKWSTRGDGL PKDTRISDSL APIGNWIRSL 2040
ELVRNQVRLN PFNEILFNQL CRTVDNHLKW SNLRRNTGMI EWINRRISKE DRSILMLKSD 2100
LHEENSWRD                                                          2109

SEQ ID NO: 4             moltype = AA  length = 883
FEATURE                  Location/Qualifiers
REGION                   1..883
                         note = T7RNAP
source                   1..883
                         mol_type = protein
                         organism = synthetic construct
SEQUENCE: 4
MNTINIAKND FSDIELAAIP FNTLADHYGE RLAREQLALE HESYEMGEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LEDTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFA                    883

SEQ ID NO: 5             moltype = AA  length = 626
FEATURE                  Location/Qualifiers
REGION                   1..626
                         note = SV40 Large T
source                   1..626
                         mol_type = protein
                         organism = Simian virus 40
SEQUENCE: 5
IPTYGTDEWE QWWNAFNEEN LFCSEEMPSS DDEATADSQH STPPKKKRKV EDPKDFPSEL  60
LSFLSHAVFS NRTLACFAIY TTKEKAALLY KKIMEKYSVT FISRHNSYNH NILFFLTPHR 120
HRVSAINNYA QKLCTFSFLI CKGVNKEYLM YSALTRDPFS VIEESLPGGL KEHDFNPEEA 180
EETKQVSWKL VTEYAMETKC DDVLLLLGMY LEFQYSFEMC LKCIKKEQPS HYKYHEKHYA 240
NAAIFADSKN QKTICQQAVD TVLAKKRVDS LQLTREQMLT NRFNDLLDRM DIMFGSTGSA 300
DIEEWMAGVA WLHCLLPKMD SVVYDFLKCM VYNIPKKRYW LFKGPIDSGK TTLAAALLEL 360
CGGKALNVNL PLDRLNFELG VAIDQFLVVF EDVKGTGGES RDLPSGQGIN NLDNLRDYLD 420
GSVKVNLEKK HLNKRTQIFP PGIVTMNEYS VPKTLQARFV KQIDFRPKDY LKHCLERSEF 480
LLEKRIIQSG IALLLMLIWY RPVAEFAQSI QSRIVEWKER LDKEFSLSVY QKMKFNVAMG 540
IGVLDWLRNS DDDDEDSQEN ADKNEDGGEK NMEDSGHETG IDSQSQGSFQ APQSSQSVHD 600
HNQPYHICRG FTCFKKPPTP PPEPET                                       626

SEQ ID NO: 6             moltype = DNA  length = 11115
FEATURE                  Location/Qualifiers
misc_feature             1..11115
                         note = Vesicular stomatitis Indiana virus strain T1026R1_
                          completesequence
source                   1..11115
                         mol_type = unassigned DNA
                         organism = Vesicular stomatitis Indiana virus
SEQUENCE: 6
tcaggagaaa ctttaacagt aatcaaaatg tctgttacag tcaagagaat cattgacaac  60
acagtcatag ttccaaaact tcctgcaaat gaggatccag tggaataccc ggcagattac 120
ttcagaaaat caaaggagat tcctctttac atcaatacta caaaaagttt gtcagatcta 180
```

-continued

```
agaggatatg tctaccaagg cctcaaatcc ggaaatgtat caatcataca tgtcaacagc    240
tacttgtatg gagccattgaa ggacatccgg ggtaagttgg ataaagattg gtcaagtttc   300
ggaataaaca tcgggaaggc aggggataca atcggaatat ttgaccttgt atccttgaaa    360
gccctggacg gtgtacttcc agatggagta tcggatgctt ccagaaccag cgcagatgac    420
aaatggttgc ctttgtatct acttggctta tacagagtgg gcgagaacaca aatgcctgaa   480
tacagaaaaa ggctcatgga tgggctgaca aatcaatgca aaatgatcaa tgaacagttt    540
gaacctcttg tgccagaagg tcgtgacatt tttgatgtgt ggggaaatga cagtaattac    600
acaaaaattg tcgctgcagt ggacatgttc ttccacatgt tcaaaaaaca tgaatgtgcc    660
tcgttcagat acggaactat tgtttccaga ttcaaagatt gtgctgcatt ggcaacattt    720
ggacacctct gcaaaataac cggaatgtct acagaagatg taacgacctg gatcttgaac    780
cgagaagttg cagatgagat ggtccaaatg atgcttccag gccaagaaat tgacaaggcc    840
gattcataca tgccttattt gatcgacttt ggattgtctt ctaagtctcc atattcttcc    900
gtcaaaaacc ctgccttcca cttctggggg caattgacag ctcttctgct cagatccacc    960
agagcaagga atgcccgaca gcctgatgac attgagtata catctcttac tacagcaggt   1020
ttgttgtacg cttatgcagt aggatcctct gctgacttgg cacaacagtt ttgtgttgga   1080
gatagcaaat acactccaga tgatagtacc ggaggattga cgactaatgc accgccacaa   1140
ggcagagatg tggtcgaatg gctcggatgg tttgaagatc aaaacagaaa accgactcct   1200
gatatgatgc agtatgcgaa acgagcagtc atgtcactgc aaggcctaag agagaagaca   1260
attggcaagt atgctaagtc agaatttgac aaaatgaccct ataattctca gatcacctat   1320
tatatattat gctacatatg aaaaaaacta acagatatca tggataatct cacaaaagtt   1380
cgtgagtatc tcaagtccta ttctcgtcta gatcaggcgg taggagagat agatgagatc    1440
gaagcacaac gagctgaaaa gtccaattat gagttgttcc aaggaggacgg agtggaagag   1500
catactaggc cctcttattt tcaggcagca gatgattctg acacagaatc tgaaccagaa    1560
attgaagaca atcaaggctt gtatgtacca gatccggaag ctgagcaagt tgaaggcttt    1620
atacaggggc ctttagatga ctatgcggat gaggacgtgg atgttgtatt cacttcggac    1680
tggaaacagc ctgagcttga atccgacgag catggaaaga ccttacggtt gacattgcca    1740
gagggtttaa gtggagagca gaaatcccag tggctttga cgattaaagc agtcgttcaa     1800
agtgccaaac actggaatct ggcagagtgc acatttgaag catcgggaga aggggtcatc   1860
ataaaaaagc gccagataac tccggatgta tataaggtca ctccagtgat gaacacacat   1920
ccgtcccaat cggaagccgt acagatgtt tggtctctct caaagacatc catgactttc     1980
caacccaaga aagcaagtct tcagcctctc accatatcct tggatgaatt gttctcatct   2040
agaggagaat tcatctctgt cggaggtaac ggacgaatgt ctcataaaga ggccatcctg    2100
ctcggtctga ggtacaaaaa gttgtacaat caggcgagag tcaaatattc tctgtagact    2160
atgaaaaaaa gtaacagata tcacaatcta agtgttatcc caatccattc atcatgagtt    2220
ccttaaagaa gattctcggt ctgaagggga aaggtaagaa atctaagaaa ttaggggatcg   2280
caccacccc ttatgaagag gacactaaca tggagtatgc tccgagcgct ccaattgaca     2340
aatcctattt tggagttgac gagagggaca ctcatgatcc gcatcaatta agatatgaga   2400
aattcttctt tacagtgaaa atgacggtta gatctaatcg tccgttcaga acatactcag   2460
atgtggcagc cgctgtatcc cattgggatc acatgtcaat cggaatggca gggaaacgtc   2520
ccttctacaa gatcttggct ttttttgggtt cttctaatct aaaaggccact ccagcggtat  2580
tggcagatca aggtcaacca gagtatcacg ctcactgtga aggcagggct tatttgccac    2640
acagaatggg gaagaccccct cccatgctca atgtaccaga gcacttcaga agaccattca   2700
atatggtct ttacaaggga acggttgagc tcacaatgac catctacgat gatgagtcac     2760
tggaagcagc tccatgatc tgggatcatt tcaattcttc caaattttct gatttcagag    2820
agaaggcctt aatgtttggc ctgattgtcg agaaaaaggc atctggagct tgggtcctgg    2880
attctgtcag ccacttcaaa tgagctagtc tagcttccag cttctgaaca atccccggtt   2940
tactcagtct ctcctaattc cagcctttcg aacaactaat atcctgtctt ttctatccct   3000
atgaaaaaaa ctaacagaga tcgatctgtt tccttgacac catgaagtgc cttttgtact    3060
tagctttttt attcatcggg gtgaattgca agttcaccat agttttttcca tacaaccaaa   3120
aaggaaactg gaaaaatgtt ccttccaatt accattattg cccgtcaagc tcagatttaa   3180
attggcataa tgacttaata ggcacagcct tacaagtcaa aatgcccaag agtcacaagg   3240
ctattcaagc agacggttgg atgtgtcatg cttccaaatg ggtcactact tgtgatttcc   3300
gctggtacgg accgaagtat ataacacatt ccatccgatc cttcactcca tctgtagaac   3360
aatgcaagga aagcattgaa caaacgaaac aaggaacttg gctgaatcca ggcttccctc   3420
ctcaaagttg tggatatgca actgtgacgg atgctgaagc agcgattgtc caggtgactc   3480
ctcaccatgt gcttgttgat gaatacacag gagaatgggt tgattcacag ttcatcaacg   3540
gaaaatgcag caatgacata tgccccactg tccataactc cacaacctgg cattccgact   3600
ataaggtcaa agggctatgt gattctaacc tcatttccat ggacatcacc ttcttctcag   3660
aggacggaga gctatcatcc ctaggaaagg agggcacagg gttcagaagt aactactttg   3720
cttatgaaac tggagacaag gcctgcaaaa tgcagtactg caagcattgg ggagtcagac   3780
tcccatcagg tgtctggttc gagatggctg ataaggatct ctttgctgca gccagattcc   3840
ctgaatgccc agaagggtca agtatctctg ctccatctca gacctcagtg gatgtaagtc   3900
tcattcagga cgttgagagg atcttggatt attccctctg ccaagaaacc tggagcaaaa   3960
tcagagcggg tcttcccatc tctccagtgg atctcagcta tcttgctcct aaaaacccag   4020
gaaccggtcc tgtctttacc ataatcaatg gtaccctaaa atactttgag accagataca   4080
tcagagtcga tattgctgct ccaatcctct caagaatggt cggaatgatc agtggaacta   4140
ccacagaaag ggaactgtgg gatgactggg ctccatatga agacgtggaa attggaccca   4200
atggagttct gaggaccagt tcaggatata agtttcctt atatatgatt ggacatggtt    4260
tgttggactc cgatcttcat cttagctcaa aggctcaggt gtttgaacat cctcacattc   4320
aagacgctgc tgcgcagctt cctgatgatg agactttatt ttttggtgat actgggctat   4380
ccaaaaaatcc aatcgagttt gtagaaggtt ggttcagtag ttggaagagc tctattgcct   4440
cttttttctt tatcataggg ttaatcattg gactattctt ggttctccga gttggtattt   4500
atctttgcat taaattaaag cacaccaaga aagacagatt ttatacagac atagagtga    4560
accgacttgg gaagtaactc aaatcctgca caacagattc ttcatgtttg aaccaaatca   4620
acttgtgata tcatgctcaa agaggcctta attatatttt aatttttaat ttttatgaaa   4680
aaaactaaca gcaatcatgg aagtccacga ttttgagacc gacgagttca tgatttcaa    4740
tgaagatgac tatgccacaa gagaattcct gaatcccgat gagcgcatga cgtacttgaa   4800
tcatgctgat tacaatttga attctcctct aattagtgat gatattgaca atttgatcag   4860
gaaattcaat tctcttccga ttccctcgat gtgggatagt aagaactggg atggagttct   4920
```

-continued

```
tgagatgtta acatcatgtc aagccaatcc catctcaaca tctcagatgc ataaatggat   4980
gggaagttgg ttaatgtctg ataatcatga tgccagtcaa gggtatagtt ttttacatga   5040
agtggacaaa gaggcagaaa taacatttga cgtggtggag accttcatcc gcggctgggg   5100
caacaaacca attgaataca tcaaaaagga aagatggact gactcattca aaattctcgc   5160
ttatttgtgt caaaagtttt tggacttaca caagttgaca ttaatcttaa atgctgtctc   5220
tgaggtggaa ttgctcaact tggcgaggac tttcaaaggc aaagtcagaa gaagttctca   5280
tggaacgaac atatgcaggc ttagggttcc cagcttgggt cctactttta tttcagaagg   5340
atgggcttac ttcaagaaac ttgatattct aatggaccga aactttctgt taatggtcaa   5400
agatgtgatt ataggaggga tgcaaacggt gctatccatg gtatgtagaa tagacaacct   5460
gttctcagag caagacatct tctccctcct aaatatctac agaattggag ataaaattgt   5520
ggagaggcag ggaaattttt cttatgactt gattaaaatg gtgaaccga tatgcaactt    5580
gaagctgatg aaattagcaa gagaatcaag gcctttagtc ccacaattcc ctcattttga   5640
aaatcatatc aagacttctg ttgatgaagg ggcaaaaatt gaccgaggta taagattcct   5700
ccatgatcag ataatgagtg tgaaaacagt ggatctcaca ctggtgattt atggatcgtt   5760
cagacattgg ggtcatcctt ttatagatta ttacgctgga ctagaaaaat tacattccca   5820
agtaaccatg aagaaagata ttgatgtgtc atatgcaaaa gcacttgcaa gtgatttagc   5880
tcggattgtt ctatttcaac agttcaatga tcataaaaag tggttcgtga atggagactt   5940
gctccctcat gatcatccct ttaaaagtca tgttaaagaa aatacatggc ccacagctgc   6000
tcaagttcaa gattttggag ataaaatggca tgaacttccg ctgattaaat gttttgaaat   6060
acccgactta ctagacccat cgataatata ctctgacaaa agtcattcaa tgaataggtc   6120
agaggtgttg aaacatgtcc gaatgaatcc gaacactcct atccctagta aaaaggtgtt   6180
gcagactatg ttggacacaa aggctaccaa ttggaaagaa tttcttaaag agattgatga   6240
gaagggctta gatgatgatg atctaattat tggtcttaaa ggaaaggaga gggaactgaa   6300
gttggcaggt agattttct ccctaatgtc ttggaaattg cgagaatact ttgtaattac    6360
cgaatatttg ataaagactc atttcgtccc tatgtttaaa ggcctgacaa tggcggacga   6420
tctaaccgca gtcattaaaa agatgttaga ttcctcatcc ggccaaggat tgaagtcata   6480
tgaggcaatt tgcatagcca atcacattga ttacgaaaaa tggaataacc accaaaggaa   6540
gttatcaaac ggcccagtgt tccgagttat gggccagttc ttaggttatc catccttaat   6600
cgagagaact catgaatttt ttgagaaaag tcttatatac tacaatggaa gaccagactt   6660
gatgcgtgtt cacaacaaca cactgatcaa ttcaacctcc caacgagttt gttggcaagg   6720
acaagagggt ggactggaag gtctacggca aaaaggatgg agtatcctca atctactggt   6780
tattcaaaga gaggctaaaa tcagaaacac tgctgtcaaa gtcttggcac aaggtgataa   6840
tcaagttatt tgcacacagt ataaaacgaa gaaatcgaga aacgttgtag aattacaggg   6900
tgctctcaat caaatggttt ctaataatga gaaaattatg actgcaatca aataagggac   6960
agggaagtta ggacttttga taaatgacga tgagactatg caatctgcag attacttgaa   7020
ttatggaaaa ataccgattt tccgtggagt gattagaggg ttagagacca agagatggtc   7080
acgagtgact tgtgtgtcacca atgaccaaat acccacttgt gctaatataa tgagctcagt   7140
ttccacaaat gctctcaccg tagctcattt tgctgagaac ccaatcaatg ccatgatcaca  7200
gtacaattat tttgggacat ttgctagact cttgttgatg atgcatgatc ctgctcttcg   7260
tcaatcattg tatgaagttc aagataagat accgggattg cacagttcta ctttcaaata   7320
cgccatgttg tatttggacc cttccattgg aggagtgtcg ggcatgtctt tgtccaggtt   7380
tttgattaga gccttccag atcccgtaac agaaagtctc tcattctgga gattcatcca    7440
tgtacatgct cgaagtgagc atctgaagga gatgatgcga gtatttgaaa acccgagat    7500
agccaagttt cgaataactc acatagacaa gctagtagaa gatccaacct ctctgaacat   7560
cgctatggga atgagtccag cgaacttgtt aaagactgag gttaaaaaat gcttaatcga   7620
atcaagacaa accatcagga accaggtgat taaggatgca accatatatt tgtatcatga   7680
agaggatcgg ctcagaagtt tcttatggtc aataaaatct ctgttccta gatttttaag    7740
tgaattcaaa tcaggcactt ttttgggagt cgcagacggg ctcatcagtc tatttcaaaa   7800
ttctcgtact attcggaact cctttaagaa aaagtatcat agggaattgg atgatttgat   7860
tgtgaggagt gaggtatcct ctttgacaca tttagggaaa cttcatttga gaaggggatc  7920
atgtaaaatg tggacatgtt cagctactca tgctgacaca ttaagataca aatcctgcgg   7980
ccgtacagtt attgggacaa ctgtacccca tccattagaa atgttgggtc cacaacatcg   8040
gaaaagaact ccttgtgcac catgtaacac atcagggttc aattatgttt ctgtgcattg   8100
tccagacggg atccatgacg tctttagttc acggggacca ttgcctgctt atctagggtc   8160
taaaacatct gaatctacat ctattttgca gccttgggaa agggaaagca aagtcccact   8220
gattaaaaga gctacacgtc ttagagatgc tatctcttgg tttgttgaac ccgactctaa   8280
actagcaatg actatacttt ctaacatcca ctctttaaca ggcgaagaat ggaccaaaag   8340
gcagcatggg ttcaaaagaa cagggtctgc ccttcatagg ttttcgacat ctcggatgag   8400
ccatggtggg ttcgcatctc agagcactgc agcattgacc aggttgatgg caactacaga   8460
caccatgggg gatctgggag atcagaattt cgactttta ttccaggcaa cgttgctcta    8520
tgctcagatt accaccactg ttgcaagaga cggatgatc accagttgta cagatcatta    8580
tcatattgcc tgtaagtcct gtttgagacc catagaagag atcaccctgg actcaagtat   8640
ggactacacg cccccagatg tatcccatgt gctgaagaca tggaggaatg gggaaggttc   8700
gtggggacaa gagataaaac agatctatcc tttagaaggg aattggaaga atttagccac   8760
tgctgagcaa tcctatcaag tcggcagatg tataggtttt ctatatggag acttggcgta   8820
tagaaaatct actcatgccg aggacagttc tctatttcct ctatctatac aaggtcgtat   8880
tagaggtcga ggtttcttaa aagggttgct agacggatta atgagagcaa gttgctgcca   8940
agtaatacac cggagaagtc tggctcattt gaagaggccg gccaacgcag tgtacggagg   9000
tttgatttac ttgattgata aattgagtgt atcacctcca ttcctttctc ttactagatc    9060
aggacctatt agagacgaat tagaaacgat tccccacaag atcccaacct cctatccgac   9120
aagcaaccgt gatatggggg tgattgtcag aaattacttc aaataccaat gccgtctaat   9180
tgaaaaggga aaatacagat cacattattc acaattatgg ttattctcag atgtcttatc   9240
catagacttc attggaccat tctctatttc caccaccctt ttgcaaatcc tatacaagcc   9300
attttatct gggaaagata gaatgagtt gagagagtcg gcaaatcttt cttcattgct   9360
aagatcagga gaggggtggg aagacataca tgtgaaattc ttcaccaagg acatattatt   9420
gtgtccagag gaaatcagac atgcttgcaa gttcgggatt gctaaggata ataataaaga    9480
catgagctat cccccttggg gaagggaatc cagagggaca attacaacaa tccctgtttta    9540
ttatcgacc accccttacc caaagatgct agagatgcct ccaagaatcc aaaatcccct   9600
gctgtccgga atcaggttgg gccagttacc aactggcgct cattataaaa ttcggagtat   9660
```

-continued

```
attacatgga atgggaatcc attacaggga cttcttgagt tgtggagacg gctccggagg  9720
gatgactgct gcattactac gagaaaatgt gcatagcaga ggaatattca atagtctgtt  9780
agaattatca gggtcagtca tgcgaggcgc ctctcctgag cccccagtg ccctagaaac   9840
tttaggagga gataaatcga gatgtgtaaa tggtgaaaca tgttgggaat atccatctga  9900
cttatgtgac ccaaggactt gggactattt cctccgactc aaagcaggct tggggcttca  9960
aattgattta attgtaatgg atatggaagt tcgggattct tctactagcc tgaaaattga  10020
gacgaatgtt agaaattatg tgcaccggat tttggatgag caaggagttt taatctacaa  10080
gacttatgga acatatattt gtgagagcga aaagaatgca gtaacaatcc ttggtcccat  10140
gttcaagacg gtcgacttag ttcaaacaga atttagtagt tctcaaacgt ctgaagtata  10200
tatggtatgt aaaggtttga agaaattaat cgatgaaccc aatcccgatt ggtcttccat  10260
caatgaatcc tggaaaaacc tgtacgcatt ccagtcatca gaacaggaat ttgccagagc  10320
aaagaaggtt agtacatact ttaccttgac aggtattccc tcccaattca ttcctgatcc  10380
ttttgtaaac attgagacta tgctacaaat attcggagta cccacgggtg tgtctcatgc  10440
ggctgcctta aaatcatctg atagacctgc agatttattg accattagcc ttttttatat  10500
ggcgattata tcgtattata acatcaatca tatcagagta ggaccgatac ctccgaaccc  10560
cccatcagat ggaattgcac aaaatgtggg gatcgctata actggtataa gcttttggct  10620
gagtttgatg gagaaagaca ttccactata tcaacagtgt ttagcagtta tccagcaatc  10680
attcccgatt aggtgggagg ctgtttcagt aaaaggaaga tacaagcaga agtggagtac  10740
tagaggtgat gggctcccaa aggataccg aatttcagac tccttggccc caatcgggaa   10800
ctggatcaga tctctggaat tggtccgaaa ccaagttcgt ctaaatccat tcaatgagat  10860
cttgttcaat cagctatgtc gtacagtgga taatcatttg aaatggtcaa atttgcgaaa  10920
aaacacagga atgattgaat ggatcaatag acgaatttca aagaaagacc ggtctatact  10980
gatgttgaag agtgacctac atgaggaaaa ctcttggaga gattaaaaaa tcatgaggag  11040
actccaaact ttaagtatga aaaaaacttt gatccttaag accctcttgt ggttttattt  11100
ttttatctgg ttttg                                                   11115
```

```
SEQ ID NO: 7              moltype = AA  length = 498
FEATURE                   Location/Qualifiers
REGION                    1..498
                          note = LCMV_GP
source                    1..498
                          mol_type = protein
                          organism = Lymphocytic choriomeningitis virus
SEQUENCE: 7
MGQIVTMFEA LPHIIDEVIN IVIIVLIIIT SIKAVYNFAT CGILALVSFL FLAGRSCGMY  60
GLNGPDIYKG VYQFKSVEFD MSHLNLTMPN ACSANNSHHY ISMGSSGLEL TFTNDSILNH   120
NFCNLTSAFN KKTFDHTLMS IVSSLHLSIR GNSNHKAVSC DFNNGITIQY NLSFSDPQSA   180
ISQCRTFRGR VLDMFRTAFG GKYMRSGWGW AGSDGKTTWC SQTSYQYLII QNRTWENHCR   240
YAGPFGMSRI LFAQEKTKFL TRRLAGTFTW TLSDSSGVEN PGGYCLTKWM ILAAELKCFG   300
NTAVAKCNVN HDEEFCDMLR LIDYNKAALS KFKQDVESAL HVFKTTVNSL ISDQLLMRNH   360
LRDLMGVPYC NYSKFWYLEH AKTGETSVPK CWLVTNGSYL NETHFSDQIE QEADNMITEM   420
LRKDYIKRQG STPLALMDLL MFSTSAYLIS IFLHLVKIPT HRHIKGGSCP KPHRLTNKGI   480
CSCGAFKVPG VKTIWKRR                                                 498
```